United States Patent [19]

Hillebrenner et al.

[11] Patent Number: 5,534,221

[45] Date of Patent: Jul. 9, 1996

[54] DEVICE AND SYSTEM FOR STERILIZING OBJECTS

[75] Inventors: H. William Hillebrenner, Apex; Vipul B. Sheth, Cary; Joseph M. Stack, Raleigh; Charles T. Curtis, Cary; Kevin H. Butler, Hillsborough; David E. Shoff, Raleigh; Robert S. Petko; William C. Little, both of Cary; Thaddeus Mielnik, Apex; Peter Zell, Raleigh, all of N.C.

[73] Assignee: American Sterilizer Company, Erie, Pa.

[21] Appl. No.: 282,228

[22] Filed: Jul. 29, 1994

Related U.S. Application Data

[63] Continuation of Ser. No. 851,096, Mar. 13, 1992, abandoned.

[51] Int. Cl.⁶ ..................................................... A61L 2/20
[52] U.S. Cl. ........................... 422/33; 422/297; 422/300; 206/438; 604/283
[58] Field of Search ............................. 422/28, 33, 292, 422/295, 300, 297; 220/4.21, 4.27, 771; 206/363, 364, 370, 438, 524.8; 600/133; 604/283

[56] References Cited

U.S. PATENT DOCUMENTS

| Re. 33,007 | 8/1989 | Bier | 203/12 |
|---|---|---|---|
| 1,683,603 | 9/1928 | Canfield | 220/4.21 |
| 2,939,603 | 6/1960 | Young | 220/4.21 |

FOREIGN PATENT DOCUMENTS

| 0302402A2 | 2/1989 | European Pat. Off. . |
| 0345713A2 | 5/1989 | European Pat. Off. . |
| 2090487A | 12/1972 | France . |
| 3334999A | 4/1985 | Germany . |
| 3334999C | 10/1986 | Germany . |
| 3820073A1 | 2/1989 | Germany . |
| 4102055A1 | 6/1990 | Germany . |
| 4003987A1 | 8/1991 | Germany . |
| 2-10505 | 1/1990 | Japan . |
| 3-68331 | 3/1991 | Japan . |
| 3-94759 | 4/1991 | Japan . |
| 3-82436 | 4/1991 | Japan . |
| 3-111026 | 5/1991 | Japan . |
| 3-123531 | 5/1991 | Japan . |
| 3-106332 | 5/1991 | Japan . |
| 3-151931 | 6/1991 | Japan . |
| 3-176061 | 7/1991 | Japan . |
| 3-176022 | 7/1991 | Japan . |
| 3-215242 | 9/1991 | Japan . |
| 3-221027 | 9/1991 | Japan . |
| 3-295535 | 12/1991 | Japan . |
| 3-280925 | 12/1991 | Japan . |
| 463240B | 10/1990 | Sweden . |
| 1519701A | 11/1989 | U.S.S.R. . |
| 1582060 | 12/1980 | United Kingdom . |
| 2052800 | 2/1981 | United Kingdom . |
| 2105591 | 3/1983 | United Kingdom . |
| 2127692 | 4/1984 | United Kingdom . |
| 2165218 | 9/1986 | United Kingdom . |
| 2191585 | 5/1987 | United Kingdom . |

OTHER PUBLICATIONS

Steris System 1™ Processor—Operator Manual, 1988, by Steris Corporation.
Instrumental In Your Practice (description of STATIM cassette, date unknown, but prior to Apr. 23, 1991.
VHP™ Technology A Collection Of Scientific Papers, First Edition Jan. 1, 1992, published by AMSCO Scientific.

*Primary Examiner*—Robert J. Warden
*Assistant Examiner*—Theresa T. Snider
*Attorney, Agent, or Firm*—Jones, Day, Reavis & Pogue

[57] ABSTRACT

A system for sterilizing an object including a hollow cassette for containing the object, a sealable opening in the cassette for ingress and egress of the object, a seal for forming a fluid-tight seal around the opening, input and output ports in the cassette for receiving and exhausting a sterilizing fluid and a sealing check valve in the input and output ports for providing a fluid-tight seal when no connections are made to the input and output ports such that when the object is sterilized within the cassette, the cassette will maintain a sterilized atmosphere for the object until the cassette is opened to allow use of the object.

7 Claims, 17 Drawing Sheets

U.S. PATENT DOCUMENTS

| | | | |
|---|---|---|---|
| 3,244,312 | 4/1966 | Lawson | 220/4.21 |
| 3,396,867 | 8/1968 | Garriga | 220/4.21 |
| 3,633,758 | 1/1972 | Morse et al. | 206/438 X |
| 4,064,886 | 12/1977 | Heckele | 134/95.3 |
| 4,169,123 | 9/1979 | Moore et al. | 422/29 |
| 4,169,124 | 9/1979 | Forstrom et al. | 422/33 |
| 4,196,166 | 4/1980 | Sanderson et al. | 422/33 |
| 4,230,663 | 10/1980 | Forstrom et al. | 422/33 |
| 4,261,950 | 4/1981 | Bainbridge et al. | 422/26 |
| 4,278,101 | 7/1981 | Tanaka et al. | 134/167 C |
| 4,281,674 | 8/1981 | Tanaka et al. | 134/95.2 |
| 4,282,179 | 8/1981 | Gunther | 422/27 |
| 4,294,250 | 10/1981 | Dennehey | 128/247 |
| 4,299,244 | 11/1981 | Hirai | 134/102.1 |
| 4,337,223 | 6/1982 | Kaye | 422/112 |
| 4,380,530 | 4/1983 | Kaye | 422/300 |
| 4,410,492 | 10/1983 | Kaye | 422/27 |
| 4,449,518 | 5/1984 | Konomura et al. | 128/4 |
| 4,489,741 | 12/1984 | Ogasawara | 134/179 |
| 4,525,220 | 6/1985 | Sasa et al. | 134/21 |
| 4,526,622 | 7/1985 | Takamura et al. | 134/21 |
| 4,526,623 | 7/1985 | Ishii et al. | 134/21 |
| 4,537,209 | 8/1985 | Sasa | 134/166 C |
| 4,579,597 | 4/1986 | Sasa et al. | 134/21 |
| 4,579,598 | 4/1986 | Sasa | 134/22.12 |
| 4,642,165 | 2/1987 | Bier | 203/12 |
| 4,648,978 | 3/1987 | Makinen et al. | 210/759 |
| 4,697,854 | 10/1987 | Lunsford | 220/4.21 |
| 4,712,657 | 12/1987 | Myers et al. | 220/4.21 |
| 4,721,123 | 1/1988 | Consentino et al. | 134/57 R |
| 4,730,729 | 3/1988 | Mönch | 206/370 |
| 4,731,222 | 3/1988 | Kravolic et al. | 422/37 |
| 4,732,187 | 3/1988 | Mönch | 134/135 |
| 4,744,951 | 5/1988 | Cummings et al. | 422/28 |
| 4,748,007 | 5/1988 | Gaudion et al. | 422/300 |
| 4,763,678 | 8/1988 | Ott | 134/171 |
| 4,843,867 | 7/1989 | Cummings | 73/29.03 |
| 4,844,052 | 7/1989 | Iwakoshi et al. | 128/4 |
| 4,862,872 | 9/1989 | Yabe et al. | 128/6 |
| 4,863,688 | 9/1989 | Schmidt et al. | 422/28 |
| 4,892,706 | 1/1990 | Kralovic et al. | 422/28 |
| 4,909,999 | 3/1990 | Cummings et al. | 422/298 |
| 4,935,371 | 6/1990 | Rickloff | 435/296 |
| 4,941,519 | 7/1990 | Sestak et al. | 141/22 |
| 4,943,414 | 7/1990 | Jacobs et al. | 422/28 |
| 4,952,370 | 8/1990 | Cummings et al. | 422/28 |
| 4,956,145 | 9/1990 | Cummings et al. | 422/28 |
| 4,973,449 | 11/1990 | Kolstad et al. | 422/27 |
| 4,998,925 | 3/1991 | Al-Sioufi et al. | 604/283 |
| 5,068,087 | 11/1991 | Childers | 422/26 |
| 5,091,343 | 2/1992 | Schneider et al. | 422/297 |
| 5,098,676 | 3/1992 | Brooks, Jr. | 422/292 |
| 5,217,698 | 6/1993 | Siegel et al. | 422/295 |
| 5,281,400 | 1/1994 | Berry, Jr. | 422/295 |
| 5,288,467 | 2/1994 | Biermaier | 422/116 |
| 5,310,524 | 5/1994 | Campbell et al. | 422/28 |
| 5,312,337 | 5/1994 | Flaherty et al. | 604/283 |
| 5,476,454 | 12/1995 | Campbell | 604/283 |

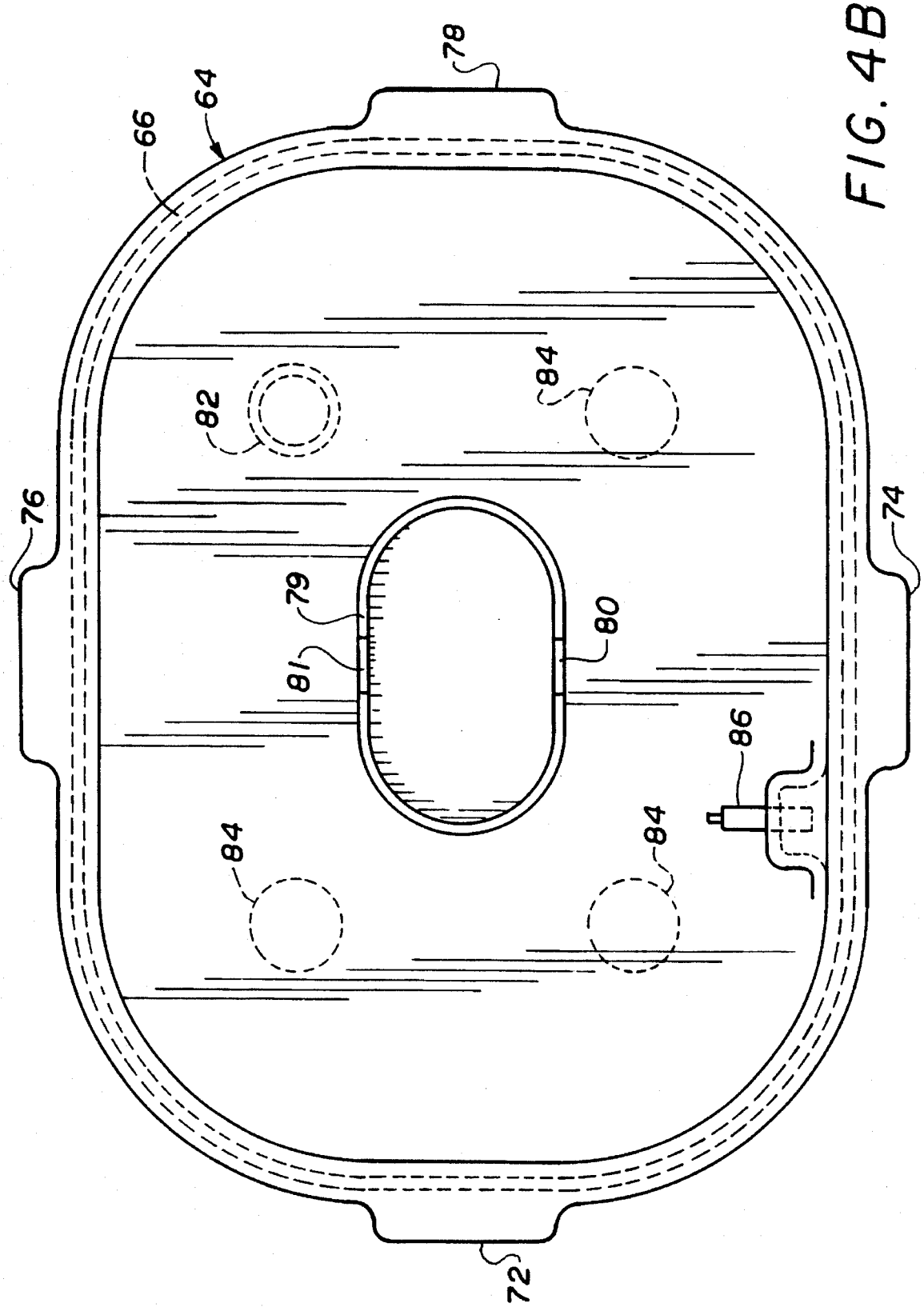

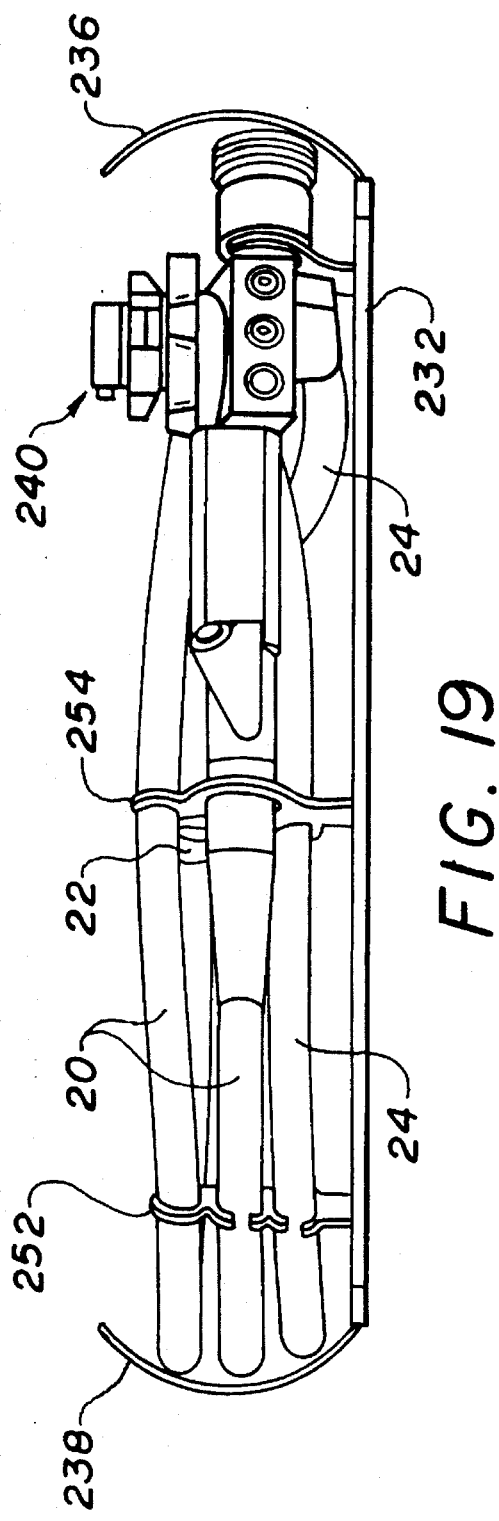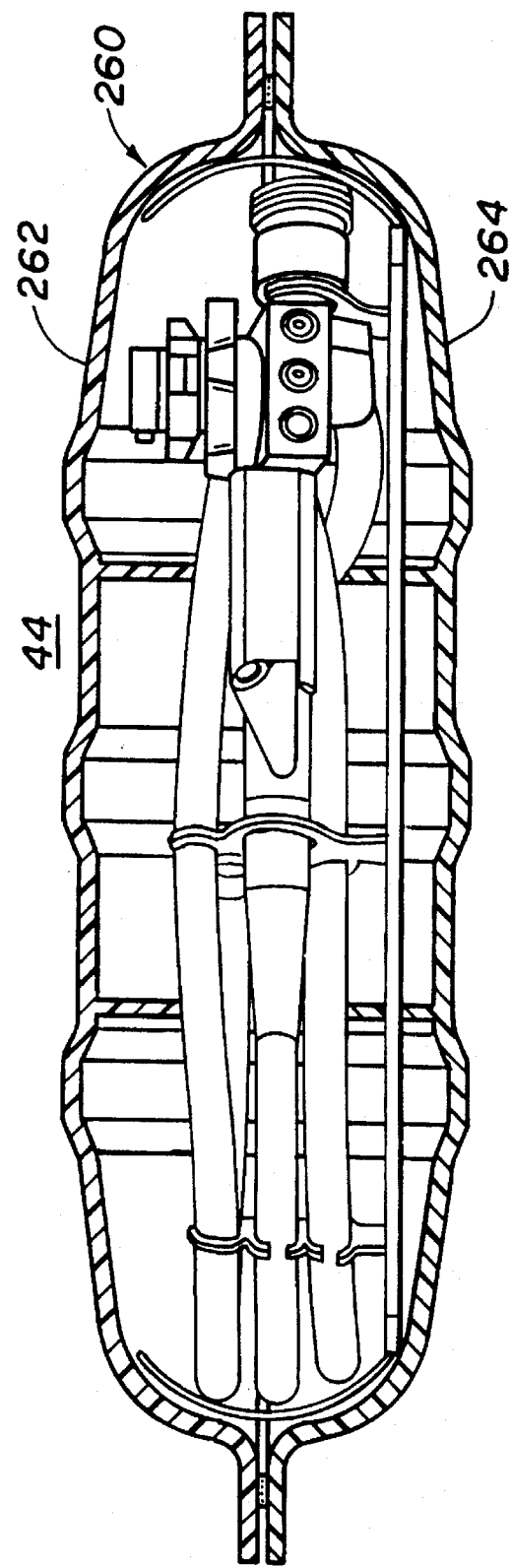

5,534,221

DEVICE AND SYSTEM FOR STERILIZING OBJECTS

This is a continuation of application Ser. No. 07/851,096 filed on Mar. 13, 1992, now abandoned.

FIELD OF THE INVENTION

The present invention relates generally to a sterilizing system and in particular to a system for sterilizing objects such as endoscopes in which the sterilized endoscope is retained within the cassette in which it was sterilized until ready for use, thus avoiding any contamination by exposure to the atmosphere or handling before use.

BACKGROUND OF THE INVENTION

Contamination by microorganisms is one of this most troublesome problems encountered today and there is often a need to sterilize devices such as medical instruments and the like.

In U.S. Pat. Nos. 4,169,123 and 4,169,124 methods are disclosed of cold gas sterilization using hydrogen peroxide gas of temperatures below 80° C. The liquid hydrogen peroxide is vaporized and the hydrogen peroxide vapor is then introduced into the sterilization chamber by pressure differential.

U.S. Pat. No. 4,642,165 discloses a method of injecting and vaporizing successive increments of a multicomponent liquid such as an aqueous solution of hydrogen peroxide, for delivery into a vacuum chamber. The vacuum in the chamber draws the multicomponent vapor into the chamber.

U.S. Pat. No. 4,512,951 discloses a method of liquid contact hydrogen peroxide sterilization. Goods to be sterilized are maintained in the sterilization chamber at a temperature below the dew point of the vapor sterilant. An aqueous solution of hydrogen peroxide is vaporized and passed into the evacuated sterilization chamber where, upon contact with the goods, the vapor condenses to form a liquid layer of sterilant on the goods. A vacuum in the chamber draws the vapor into the chamber.

United Kingdom Patent No. 1,582,060 discloses a similar liquid contact hydrogen peroxide sterilization method operated without a vacuum chamber. Liquid hydrogen peroxide is pumped through an ultrasonic spray nozzle which is operated by a stream of dehydrated air. A mist of hydrogen peroxide is sprayed into a container and mixed with hot air to change the mist into a vapor. The vapor is piped into a nonpressurized sterilization chamber where it condenses on a cool moving web of material. A stream of hot air in an adjacent chamber removes the hydrogen peroxide layer from the web. The stream is then passed to a water separator where it is relieved of the sterilant.

In some other prior art systems, when the object such as a medical instrument has been sterilized, it must be removed from the sterilization chamber and handled in some form to be prepared for and transported to the medical facility for use. For instance, with the use of endoscopes which have multiple hollow tubes therein for air, water, vacuum and the like, the endoscope is placed in a container and input and output fluid connections are made to the appropriate endoscope connections and the chamber is sealed. A sterilizing fluid is introduced into the chamber through one port where it not only surrounds and bathes the endoscope with the sterilizing agent, but is also passed through the hollow tubes of the endoscope by applying a vacuum on the other port, thus sterilizing the interior of any tubes.

However, the endoscope may still have moisture on it and the ambient air may then enter the chamber after the sterilization process or the endoscope may simply be removed from the chamber and placed in ambient air so that it will dry before use.

Such a system is inherently dangerous since any handling of the endoscope after sterilization or exposing it to ambient air after sterilization provides opportunity for recontamination of this endoscope. Further, it may continue to have moisture on the interior thereof which may contain contaminants that could be injected into the next patient with whom the endoscope is to be used.

These disadvantages of the prior art are overcome by the present invention which includes a sealable cassette in which the endoscope or other medical device is placed. The cassette has input and output fluid sealing ports for the introduction and removal of a sterilizing fluid. The endoscope or other medical instrument, if hollow, is coupled either to the input or output port. The cassette is formed of two identical halves which are placed in superimposed sealable relationship with each other to form a hollow chamber. A latch is placed on one or more handles on the cassette to create a presealing condition to allow a vacuum to be introduced at the outlet port.

The cassette is then placed in an outer oven-like container or warming chamber where the temperature is properly maintained. Connections are made to open the input and output ports on the cassette such that the sterilizing agent may be introduced through a first port to bathe the outside of the medical instrument or other object, such as an endoscope, while one end of the hollow object, such as the endoscope, is coupled to the output port where a vacuum is supplied external to the cassette to pull the sterilization agent into the cassette and through the interior passageways of the endoscope. When the sterilization process is completed, the warming chamber is opened and the sterilizing cassette is simply removed from the chamber with the input and output ports being uncoupled from their respective sources. A tight seal is maintained and the object remains in the sterilized interior of the cassette until the cassette is opened or the device is to be used. It can be stored, transported and handled without adversely affecting the sterilization of the object therein.

The two identical halves of the cassette may be bowl shaped for mating contact with each other to form the hollow chamber. A center support device formed in each bowl-shaped container section for mating contact with the center support of the mating bowl-shaped container section to prevent opposing container walls from collapsing under a vacuum. The bowl-shaped container sections can be one piece molded from a clear plastic so that the object contained therein can be observed without breaking the fluid-tight seal. The clear plastic can be a polycarbonate such as a product sold under the trademark "LEXAN". The center support means may have a hollow oval shape so that small objects such as endoscope parts could be placed therein. The oval support has an opening therein allowing the sterilizing agent to pass into it assuring sterilization of all internal surfaces and for sterilizing the small endoscope parts which may be placed therein. The center support means could be a hollow cylindrical shape or a solid cylindrical shape if desired. Each of the bowl-shaped container sections has a port with a check valve therein for providing a fluid seal that can be opened to deliver or receive a sterilizing fluid or provide a means of evacuation and closed to provide a fluid-tight seal to maintain sterilization within the cassette after the sterilization process is completed.

The cassette may also have first and second spaced concave and convex dimples on the external surface of the cassette outer walls such that when one cassette is stacked on another, the convex dimples on one cassette outer wall mate with the concave dimples on the other cassette outer wall so as to enable the cassettes to maintain their stacked relationship. A flat surface is formed around the perimeter of each cassette container section. A compressible seal is placed on the flat surface perimeter and at least one seal causing device is associated with the first and second container sections for forcing the container sections toward each other to compress the seal and form a fluid-tight seal between the first and second container sections. The container sections may also have a plurality of spaced convex ribs formed on the outer side of each molded container wall to strengthen the container walls to resist collapsing under a vacuum.

Some objects such as endoscopes have multiple elongated lumens with each lumen having a proximal end terminating in a port and a distal end. A connector is used inside the cassette to couple the proximal end ports of the lumens to one of the input and output ports on the interior of the cassette such that a sterilizing fluid passing from the input port to the output port passes through the lumens of the endoscope for complete sterilization.

Further, a tray is formed for holding the endoscope in the cassette. Clip devices are attaches to the tray to hold the outside surfaces of the endoscope in spaced relationship with each other to minimize contact area thereby facilitating sterilization. The tray can be formed of a flat plastic or metal sheet with an orifice in the flat sheet for receiving the cassette center support device and opposing handles are formed on the tray for handling the tray.

It is an object of the present invention to provide a system for sterilizing an object within a closed cassette such that when the sterilization process is completed, the sterilized object remains in the sealed cassette until use is required, thus maintaining the unit in its sterilized condition during storage.

It is also an object of the present invention to provide a novel cassette for storing the object to be sterilized during the sterilization process and for maintaining the sterilization of the device within the cassette after the sterilization process completed.

It is yet another object of the present invention to provide a connector for connecting the fluid ports of an object such as an endoscope to one of the input and/or output ports on the interior of the cassette such that when the cassette is sealed and a sterilization fluid is passed from the input port to the output port, the object is sterilized both internally and externally by causing the sterilization fluid to flow through the lumens of the object.

It is still another object of the present invention to provide a tray for insertion in the cassette such that the surface of an object is maintained in spaced relationship to minimize the sterilization contact area thereby facilitating sterilization.

SUMMARY OF THE INVENTION

Thus, the present invention relates to a device for sterilizing endoscopes comprising a cassette containing the endoscope to be sterilized, an access section in the cassette in fluid-tight relationship with the remainder of the cassette, an input port the cassette for receiving a sterilizing agent through a connector, an output port in the cassette for expelling the sterilizing agent when a vacuum is applied thereto through a connector, and check valves in the cassette input and output ports to open the ports when the connectors are coupled to the ports and to seal the ports when the connectors are removed from the ports such that after the endoscope has been sterilized, it remains sterilized within the cassette until the cassette access section is opened.

The invention also relates to a system for sterilizing an object comprising a hollow cassette for containing the object, the cassette having an opening section for ingress and egress of the object, sealing means for forming a fluid-tight seal around the opening section, input and output ports in the cassette for receiving and exhausting a sterilizing fluid, and a sealing check valve in the input and output ports for providing a fluid-tight seal when no connections are made to the input and output ports such that when the object is sterilized within the cassette, the cassette will maintain a sterilized atmosphere for the object until the cassette opened to allow use of the object.

BRIEF DESCRIPTION OF THE DRAWINGS

The objects of the invention will be more fully understood when taken in conjunction with the accompanying detailed description of the drawings in which like numerals represent like elements and in which:

FIG. 4B is a plan view of the interior of one-half of the cassette;

FIG. 19 is a side view of the tray holding the endoscope of FIG. 18;

FIG. 21 is a side view of a closed cassette formed of clear plastic illustrating within the cassette, the tray holding the endoscope.

DETAILED DESCRIPTION OF THE DRAWINGS

Figure 1:
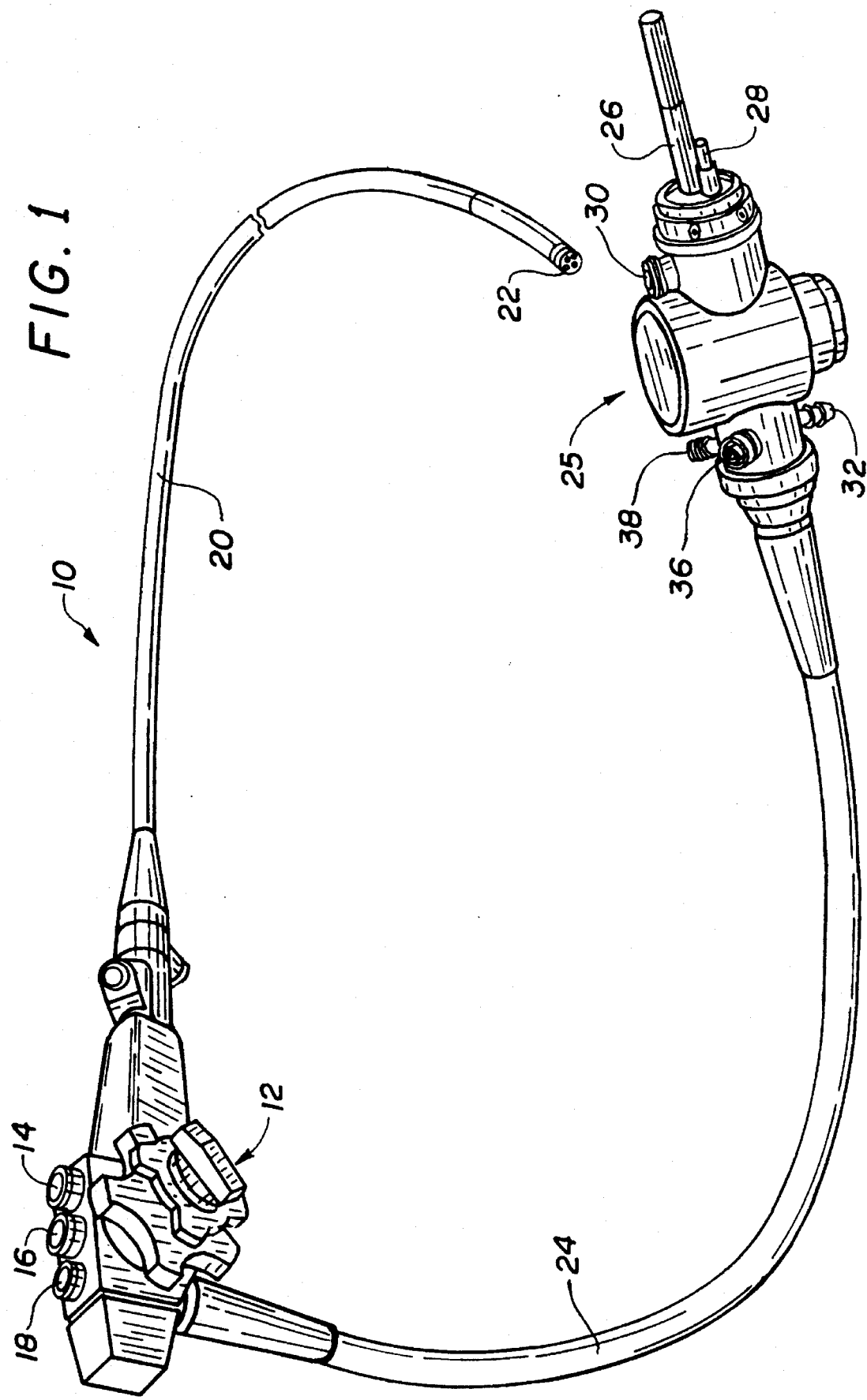
FIG. 1 is a drawing of an endoscope that can be sterilized with the present invention.

The endoscope 10 illustrated in FIG. 1 has a control section 12 with the air/water valve 14 which, when its valve cover (not shown) is depressed, activates water feeding to the distal end 22 of the insertion tube 20. The suction valve 16, when its valve cover (not shown) is depressed, activates suction from the distal end 22 of tube 20 and $CO_2$ gas valve 18, when depressed, connects lumens in the control section that insufflate noncombustible gas into the body cavity. The insertion tube 20 is inserted in the body cavity and the operator, using the control section 12, controls the flow of air, water, suction and gas to and from the body cavity.

The universal cord 24 couples the control section 12 to the light guide connector section 25 that has light guide 26 to be connected to a light source, an air pipe 28 and a water container connector 30 also has a suction connector 32 and other connectors 36 and 38 for such functions as a gas tube connector and a vent connector.

Figure 2:
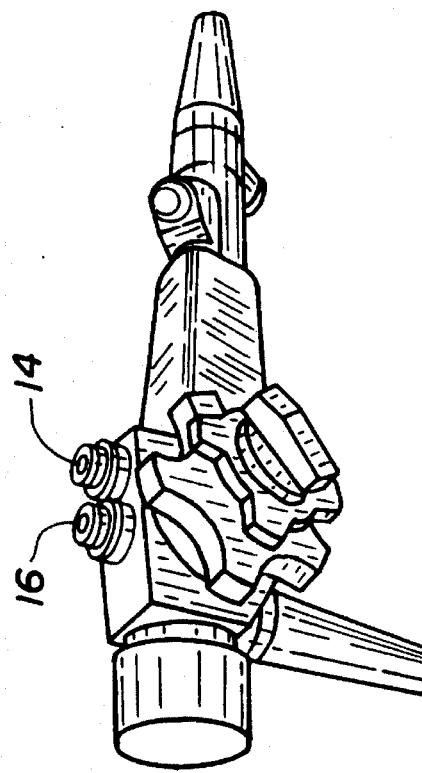
FIG. 2 is a partial diagram of a two-port endoscope that can be sterilized by the present invention.

FIG. 2 is a partial view of an endoscope which does not have the C02 valve 18 shown in FIG. 1. Otherwise, the units are substantially identical. In use, the endoscopes of FIG. 1 and FIG. 2 have the insertion tube 20 inserted in a body cavity and fluids are coupled to and from the body cavity. Thus, the unit must be completely cleansed and sterilized after use. In order to sterilize the lumens of the insertion tube 20 and the universal cord 24, the sterilizing agent must not only sterilize the outside of the endoscope but also must pass through the lumens to sterilize the interior thereof.

Figure 3:
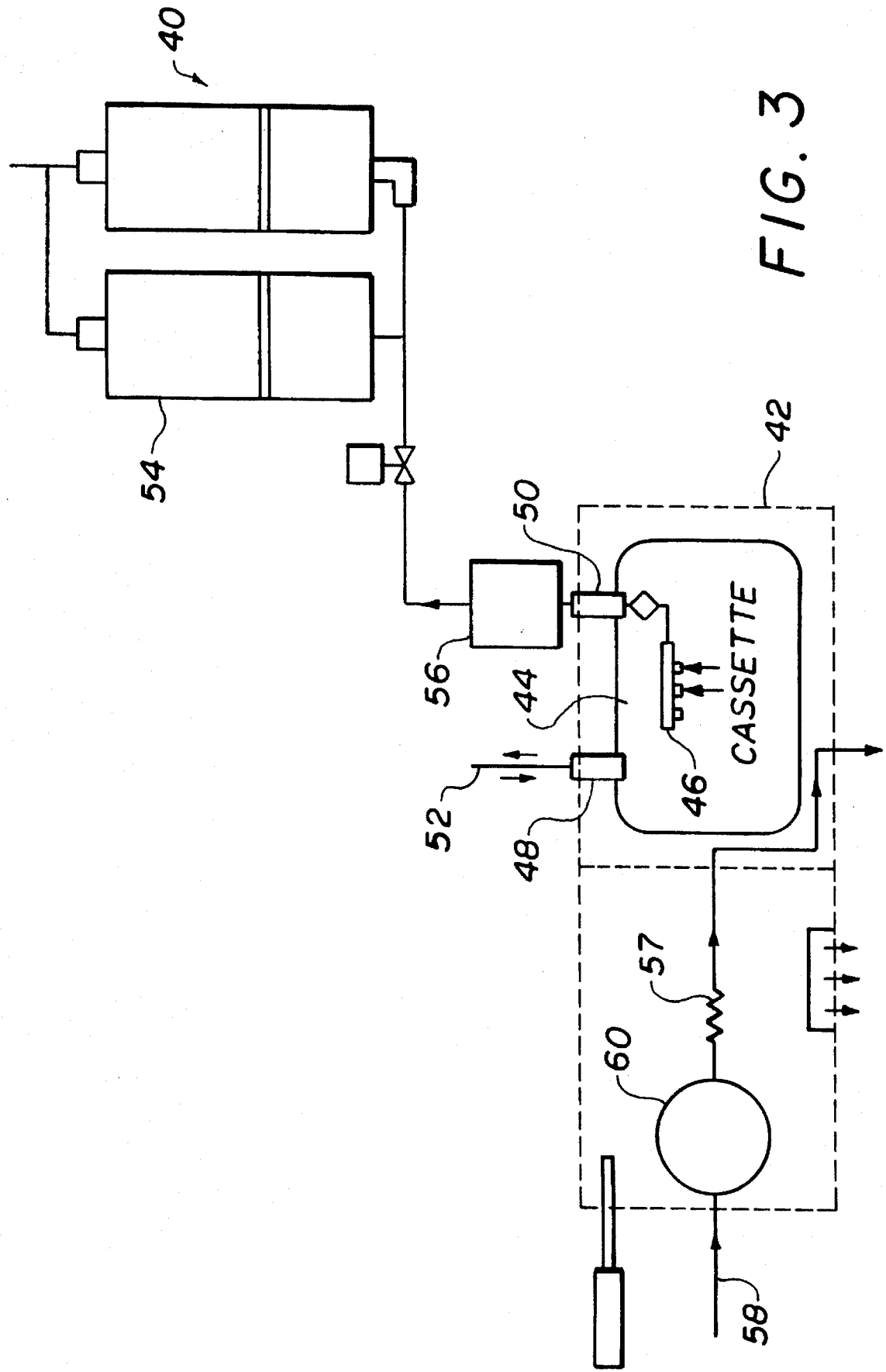
FIG. 3 is a schematic representation of the sterilization system of the present invention.

A system for sterilizing an object such as all endoscope is shown in FIG. 3. The system 40 comprises a warming cabinet or container 42 that receives a cassette 44 in which is mounted an endoscope such as shown in FIGS. 1 and 2. The endoscope ports 14 and 16 are coupled by means of a connector 46 to an outlet port 50 in the cassette 44. A sterilizing agent in the form of a sterilizing gas is prepared as disclosed in commonly assigned copending application Ser. No. 7/850,941 and entitled "Method of Detecting Liquid in Sterilization System", which disclosure is incorporated herein by reference in its entirety, and thus will not be disclosed in any detail herein. The sterilizing agent is coupled through a conduit 52 to an inlet port 48 in the cassette 44. The interior of the cassette is then filled with the sterilizing agent and surrounds and sterilizes the exterior of the object therein such as an endoscope. By applying a vacuum from source 54 through outlet port 50, the sterilizing agent inside the cassette 44 is forced through the lumens on the interior of the object such as the endoscope, thus sterilizing the interior thereof. It should be noted that the inlet and outlet ports also provide a means to supply and remove air and/or other fluids to and from the cassette during other phases of the process, such as warm-up and aeration. A unit 56 can contain pressure sensors and temperature sensors to monitor pressure, temperature, and water content inside the cassette. This unit is also discussed in the commonly assigned copending application set forth previously and so will not be discussed here. The cassette cabinet or container 42 is maintained in predetermined environmental condition by a heater warming input air from conduit 58 and being forced by a blower 60 into the cassette cabinet 42 to maintain the temperature at a proper temperature therein. The endoscope may be placed on a tray such as that shown in FIGS. 17–21 before being placed in the cassette 44 in order to maintain a separation between the coiled endoscope insertion tube and universal cord to minimize contact areas of the tubes and maximize the exposed areas to be sterilized.

Figure 4A:
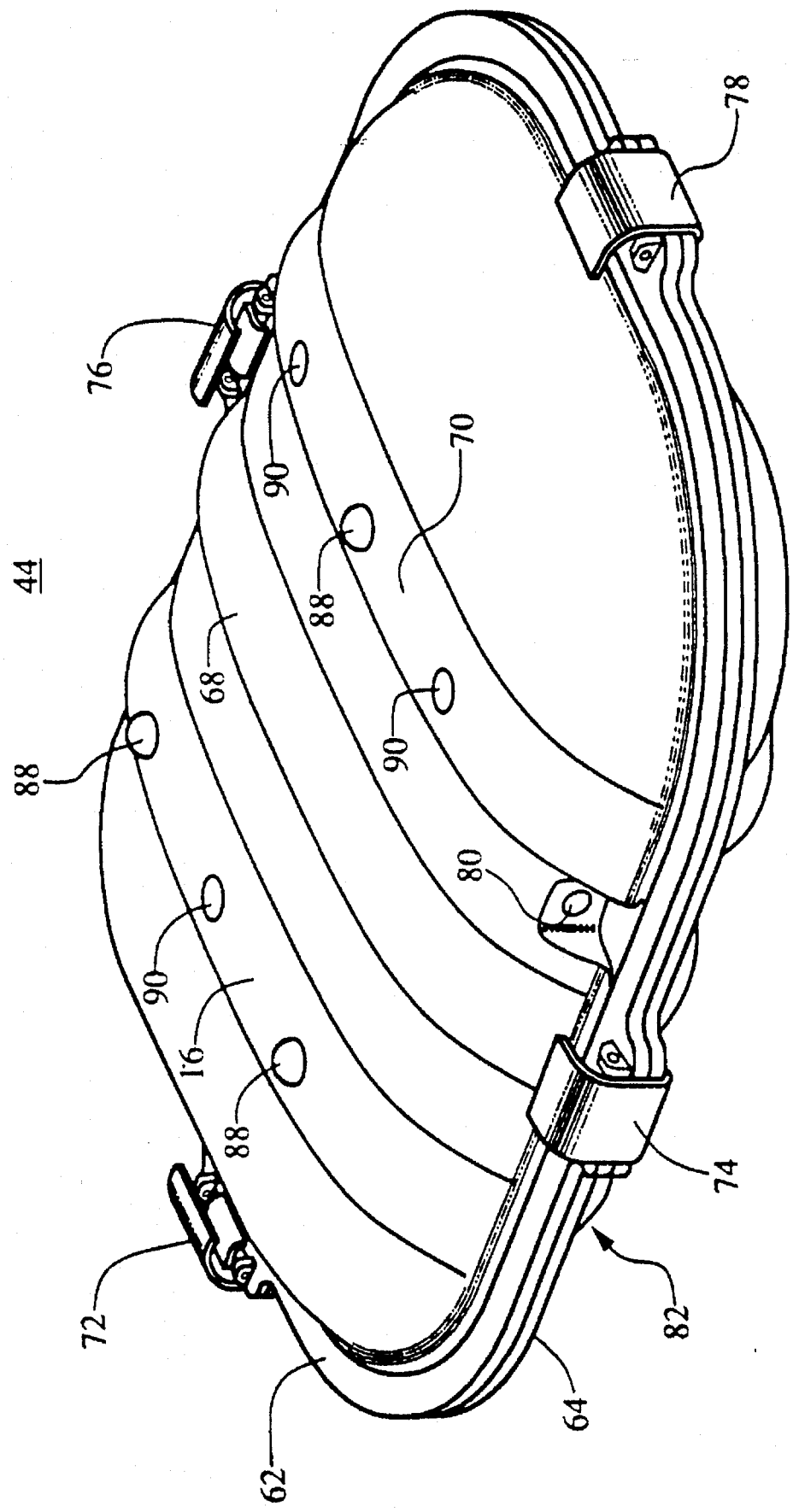
FIG. 4A is a perspective view of a cassette in its sealed condition.

The novel cassette 44 used in the system of FIG. 3 is illustrated in FIG. 4A in an isometric view of the sealed cassette. In the preferred embodiment, it is comprised of two identical generally bowl-shaped sections 62 and 64 which, when placed in abutting relationship as shown, form the cassette 44 of the present invention. It should be noted that the invention does not require that the cassette be constructed of identical halves. It has strengthening ribs 66, 68 and 70 and sealing handles 72, 74, 76 and 78. These handles are disclosed in detail in commonly assigned copending application Ser. No. 851,487, filed Mar. 13, 1992, and entitled "Cassette for Sterilizing Articles and Latch Therefor", which disclosure is incorporated herein by reference in its entirety, and thus will not be disclosed in any detail herein. It has an inlet port 80 and an outlet port 82 in which well-known check valves are inserted so that when connections are made to the input and output ports the sterilizing agent can flow though the input port into the cassette, surround and pass through the endoscope tubes and lumens and out the output port. Yet, when the connectors are removed from the input and output ports, the check valves seal the cassette with a fluid-tight seal to prevent contamination external to the cassette from entering the cassette, and can also maintain a differential in pressure, if existing, between the inside and outside of the cassette.

FIG. 4B is a plan view of one-half of the cassette illustrating the interior thereof. The separable section shown in FIG. 4B may be the lower half 64 of the cassette 44 in FIG. 4A. It has a flat surface around the perimeter of the section 64 with a compressible seal 66 placed thereon. When the handle closing devices 72, 74, 76 and 78 in FIG. 4A are closed, they force the container sections 62 and 64 toward each other to compress the seal 66 and form a fluid-tight seal between the first and second container sections 62 and 64. A center support 79 is formed in each bowl-shaped container section for mating contact with the center support of the other bowl-shaped container section to prevent opposing cassette walls from collapsing under a vacuum. It should be noted that in the case where the cassette halves are not identical, the center support could be formed entirely in one of the container sections, or each of the sections could have supports which are different in construction. The bowl-shaped sections 62 and 64, in one example, are each molded in one piece from a clear plastic such as a polycarbonate sold under the trademark "LEXAN" so that the object contained within the cassette can be observed without breaking the fluid-tight seal. Clearly, the cassette could also be constructed to have only portions of the outer walls clear for observation of the contents. The center support 79, in the preferred embodiment, is a hollow oval shape as shown such that small endoscope parts could be placed therein for sterilization. The oval support has an opening 81 and 80 therein for enabling the sterilizing agent to enter the oval-shaped support means to sterilize all internal surfaces and the parts that might be contained therein. Thus, the center support means 76 has two functions: first, to provide a support font preventing the two cassette halves from collapsing against each other when a vacuum is applied thereto and, second, to provide an area where small parts can be placed and sterilized. The center supports, if desired, could be cylindrical in shape as illustrated in phantom lines 82 and placed in the center or other areas. It could also be a solid cylindrical shape such as shown by phantom lines 84.

As stated previously, each of the cassette sections 62 and 64 includes a well-known check valve 86 in the port therein for providing a fluid seal that can be opened to deliver or receive a fluid and closed to provide a fluid-tight seal to ensure sterilization in the cassette after the sterilization process is completed. Referring again to FIG. 4A, first and second spaced convex and concave dimples 88 and 90 are formed on the external surface of cassette outer walls such that when one cassette is stacked on another, a convex dimple 88 on one cassette outer wall mates with a concave dimple 90 on the adjacent cassette outer wall so as to enable the cassettes to maintain their stacked relationship.

Figure 4C:
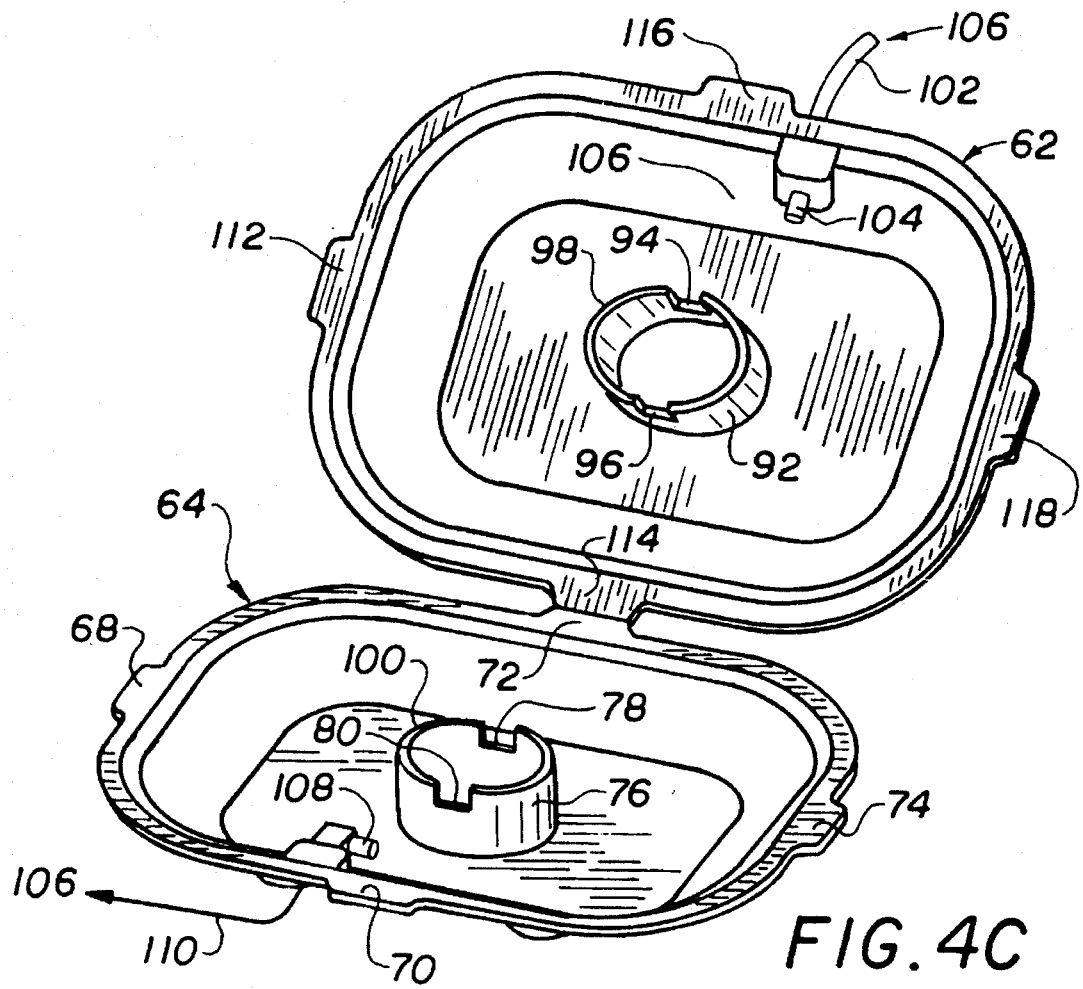
FIG. 4C is an isometric view of both halves of the cassette.

A perspective view of the two bowl-shaped container section halves 62 and 64 is illustrated FIG. 4C in their open position. The oval center support means 76 in cassette half 64 with its opening 78 and 80 can be seen in FIG. 4C. Bowl-shaped container section 62 also contains a mating half of an oval support means 92 having openings 94 and 96 therein. When the two halves 62 and 64 are placed together in facing relationship, the edges 98 and 100 of the center supports 79 and 92 are in superimposed, spaced relationship with each other such that when a vacuum is applied to the container it pulls the two sides of the bowl-shaped sections 62 and 64 toward each other and the edges 98 and 100 meet to form a support to prevent the two outer walls of the sections 62 and 64 from collapsing. For example, in one embodiment constructed, the thickness of the cassette halves was ³⁄₁₆", the center supports were of thickness ¼", and a vacuum level of 1 mm of absolute was applied, sufficient to perform sterilization cycle. As stated earlier, in addition, the orifices formed by the openings 81 and 96 and 80 and 94 allow the sterilizing agent to reach any objects that may be placed in the oval-shaped supports 79 and 92 to sterilize them. The sterilizing agent enters conduit 102 through the check valve and through an outlet valve 104 which, in one example, has orifices therein to direct the fluid flow in the direction illustrated by arrows 106. This causes the sterilizing agent to circulate around the periphery of the interior of the cassette to provide a generally circular flow of the sterilizing agent for maximum distribution. The sterilizing agent or fluid passes through the lumens of the endoscope as described earlier and to a connector, such as shown in FIG. 7 or FIG. 14, which is coupled to tube 108 in FIG. 4C where it passes through the check valve and out on line 110 to the vacuum source. Conversely, the endoscope could be coupled to the input port, in which case the sterilizing agent passes through the internal lumens of the endoscope, into the interior of the cassette and through the output port to the vacuum source. However, for simplicity of explanation, hereafter reference will be made only to the endoscope coupled to the output port. The handle sections 112, 116, 114 and 118 in cassette section 62 are in superimposed relationship with corresponding handles 68, 70, 72 and 74 on the lower bowl-shaped section 64 when the two sections are placed in a face-to-face abutting relationship. Thus, each pair of handle sections, such as 68 and 112, form a cassette handle. The other pair in like manner form cassette handles. The handles have sealing devices thereon and are formed as disclosed in commonly assigned copending application Ser. No. 857,487, incorporated herein as set forth earlier.

Figure 5:
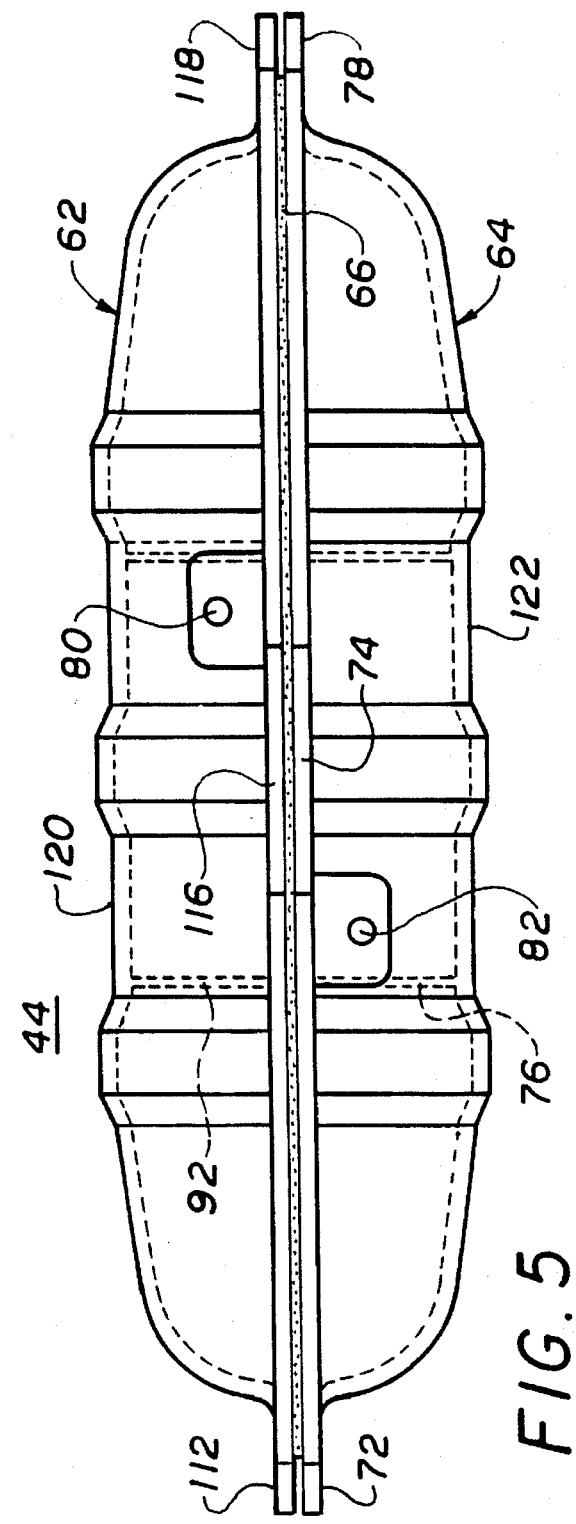
FIG. 5 is a side view of the entire cassette in FIG. 4A.
Figure 6:
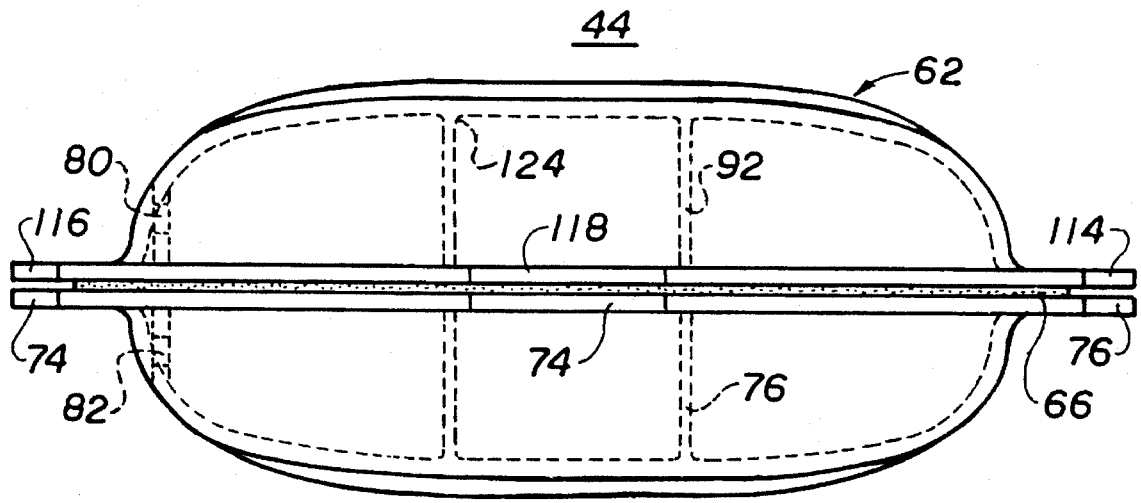
FIG. 6 is an end view of the cassette in FIG. 4A.

FIG. 5 is a side view of the cassette 44 illustrating the two identical generally bowl-shaped container sections 62 and 64 having outer walls 120 and 122 which, as can be seen in FIG. 5 when placed in face-to-face relationship, form a hollow chamber for receiving the endoscope. The input port 80 and the output port 82 can be clearly seen. In addition, the handle sections 68 and 112, 70 and 116, and 74 and 118 can be seen in abutting relation such that each of the pairs forms a cassette handle. The seal 66 can be seen in the perimeter of the cassette 44. In addition, the oval-shaped center supports 76 and 92 can be seen in phantom lines. The seal 66 between the sections 62 and 64 can be seen. An end view of the cassette 44 is illustrated in FIG. 6. Again, the abutting relationship of the handle portion 70 and 116, 74 and 118, and 72 and 114 can be seen. Also, the input port 80 and the output port 82 can be seen. The oval-shaped center supports 76 and 92 can be seen in phantom lines. The center supports are integrally formed at 124 with the bowl-shaped sections 62 and 64. The seal 66 can also be seen.

In order to couple the endoscope ports to the inlet or outlet port of the cassette, the operating caps for each of the ports 14, 16 and 18 shown FIG. 1 must be removed as is illustrated in FIG. 1. This exposes the ports. Then the connector illustrated generally in FIG. 3, is coupled to the ports in a fluid-tight relationship. The connector 46 in FIG. 3 is a hollow housing for sealably surrounding the endoscope terminating ports 14 and 16 and opening the $CO_2$ valve 18 if present as shown in FIG. 1. The connector 46 provides a quick disconnect for coupling a hollow housing therein to the endoscope ports 14 and 16 in fluid-tight, fluid-transfer relationship. A conduit couples the interior of the connector housing to the inlet or outlet port on the interior of the cassette. Such conduit is illustrated in FIG. 4C at 108.

Figure 9:
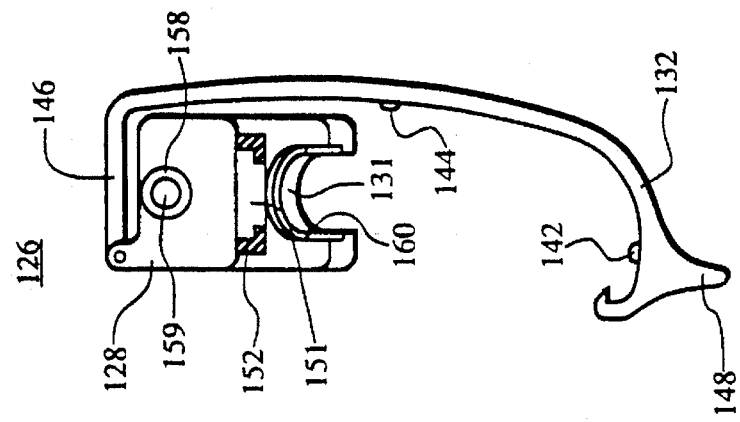
FIG. 9 is a rear view of the connector of FIG. 7.
Figure 8:
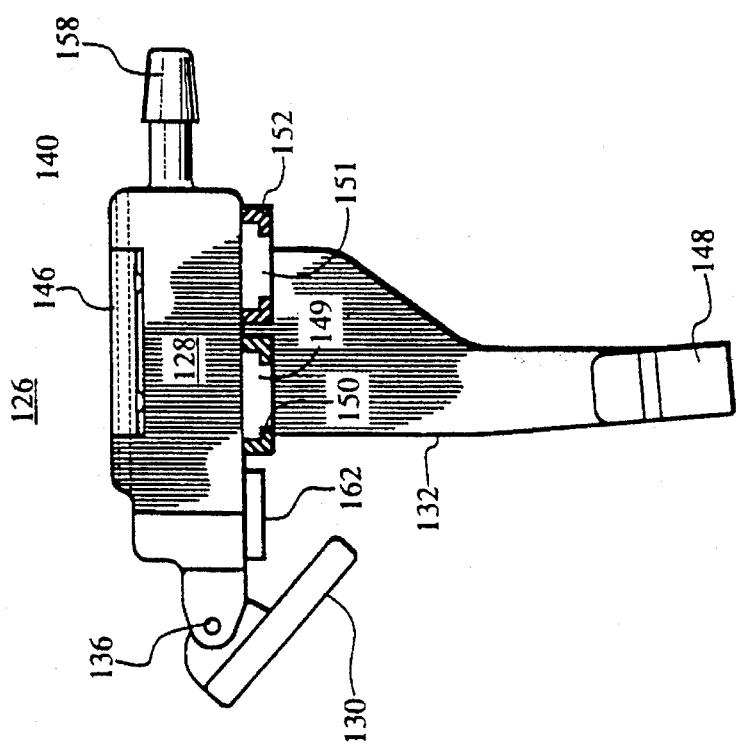
FIG. 8 is a side view of the connector of FIG. 7.
Figure 7:
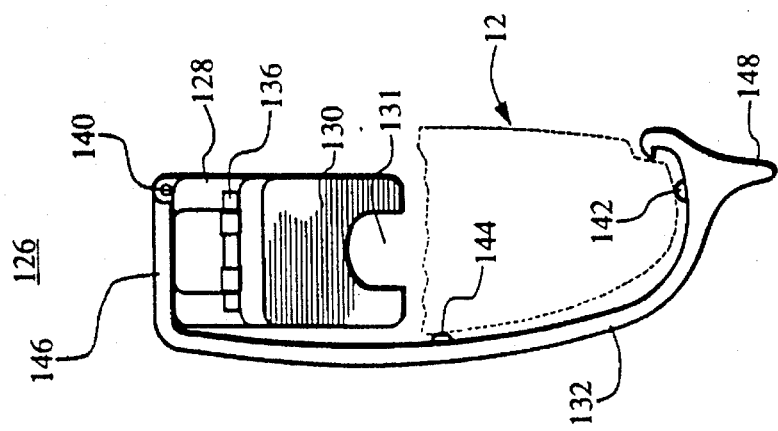
FIG. 7 is a front view of a connector for forming a quick disconnect to connect the ports of the endoscope to an interior port of the cassette.
Figure 10:
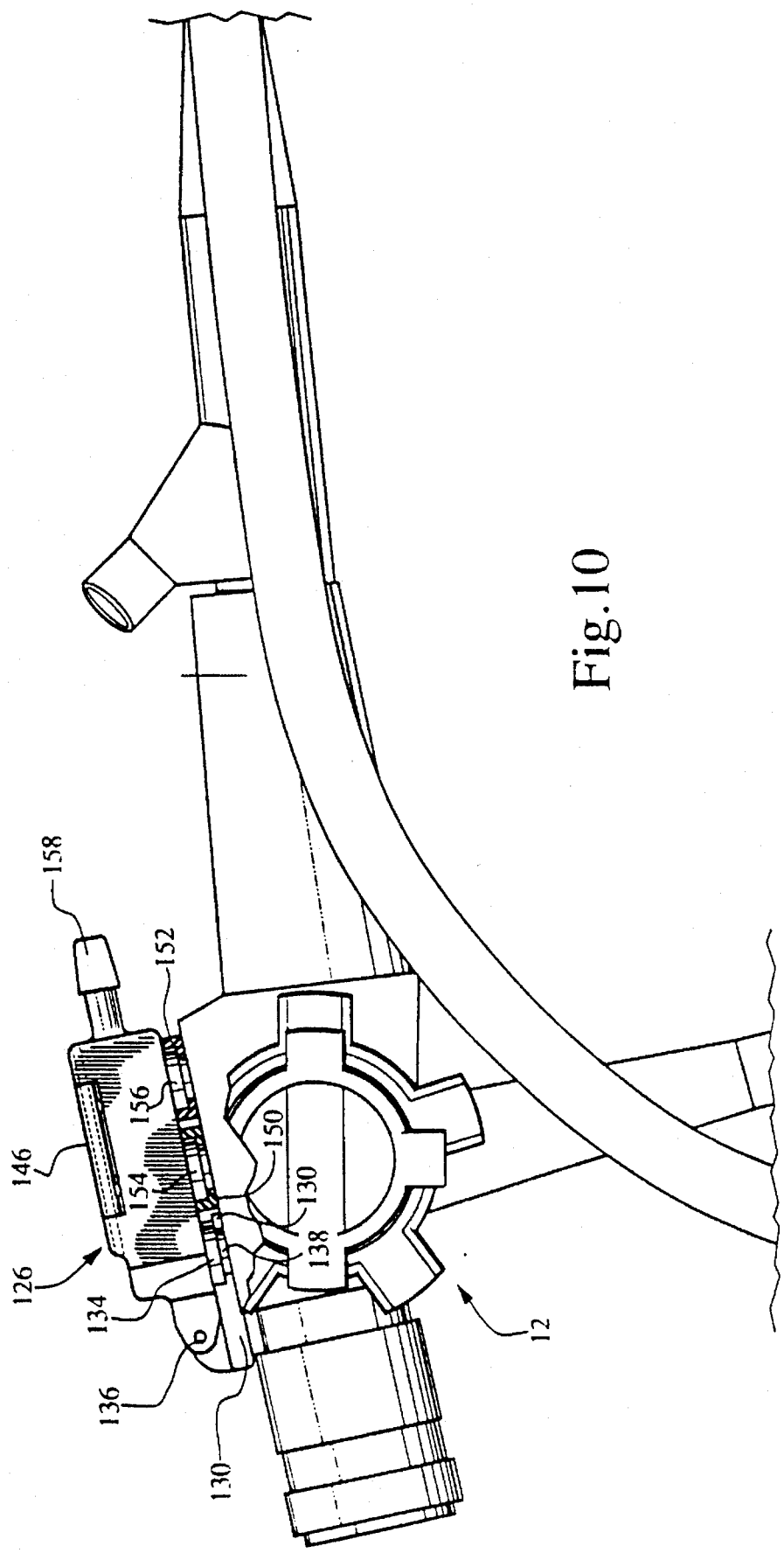
FIG. 10 is a representation of the connector of FIG. 7 attached to a three-port endoscope.

One connector embodiment is illustrated in FIGS. 7, 8 and 9. FIG. 7 is a front view of the connector embodiment designated by the numeral 126. The connector 126 has a hollow housing 128 for sealably enclosing the ports 14 and 16 on the endoscope and a fastener means 130 for slidable attachment of the housing 128 to at least one of the endoscope ports and in particular to the $CO_2$ port 18 as shown in FIG. 1. The U-shaped opening 131 allows the fastener 130 to slide under a flange 134 of the $CO_2$ port as shown in FIG. 10. A pin 136 pivotally attaches the fastening device 130 to the housing 128. A locking means 132 locks the housing 128 in a sealed fluid-tight, fluid-transfer relationship to the endoscope ports 14 and 16. Each endoscope port has a neck portion 138 as illustrated in FIG. 10 with the flange 134 at the top thereof. The flange has a diameter larger than the neck portion 138 and the diameter of opening 131 in the fastener means 130 in FIG. 7 simply slides under flange 134 and around neck 138 of the $CO_2$ port, thus slideably attaching the fastener to the $CO_2$ port, as illustrated in FIG. 10.

The locking device 132 is a J-shaped extension that is pivotally coupled to the housing 128 by pin 140 and extends down the side and under the control section 12 of the endoscope. The J-shaped extension 132 is formed of a pliable plastic that has sufficient resiliency to bend under and grip the body portion of the control section 12 to hold the housing 128 in fluid sealing engagement with the ports 14 and 16. Spaced apart point contact protrusions 142 and 144 on the inside of the J-shaped extension 132 minimize contact of the extension 132 with the endoscope body and thus maximize the area to be sterilized. A horizontal arm 146 extends across the top of the housing 128 from the j-shaped extension 132 for pivotal attachment at pin 140 to the housing 128 such that the horizontal arm 146 exerts a downward pressure on the housing 128 when the J-shaped extension 132 is under and gripping the endoscope body portion 12. A downwardly extending projection 148 at the bottom of the J-shaped extension 132 provides a finger grip for easy removal of the J-shaped extension 132 from under the endoscope body portion 12.

FIG. 8 is a side view of the connector illustrated in FIG. 7. The body portion 128 is a hollow housing having fluid connection with ports 149 and 151. Each of the ports has a rubber seal, 150 and 152, as illustrated in FIG. 8, that mates with and under flanges 154 and 156 on the ports 14 and 16 as illustrated in FIG. 10. Also, an extension 158 which has an orifice 159 therein is coupled to the interior of the hollow housing 128 can be coupled to a suction source to pull the sterilizing agent through the lumens of the endoscope, through endoscope ports 14 and 16 and connector ports 149 and 151 and out the orifice 159 in extension 158 to the vacuum source. Depressor 162 is used with the $CO_2$ port 18 on the endoscope to depress the poppet valve therein such that when the housing 128 is in sealable engagement with the endoscope ports 14 and 16, the valve depressor 162 opens the $CO_2$ valve 18 which forms lumen connections within the endoscope.

FIG. 9 is a rear view of the connector illustrated in FIG. 8 and shows the orifice 159 which is coupled to the interior of housing 128 and which can be coupled to the vacuum source through the output port of the cassette. It also has a ledge 160 in the U-shaped opening 131 of fastening means 130 which receives the flange 134 on the $CO_2$ port as illustrated in FIG. 10. FIG. 10 illustrates a three-port endoscope with the connector 126 mounted thereon. The connector 126 is illustrated in phantom lines to clearly show the flanges 134, 154 and 156 of the respective ports 18, 16 and 14 in FIG. 1. It also illustrates how the rubber seals 150 and 152 the housing 126 surround the flanges 154 and 156 to form a fluid-tight seal. It also illustrates how the fastening device 130 slides under the flange 134 of the poppet of the $CO_2$ port 18 in FIG. 1.

Figure 11:
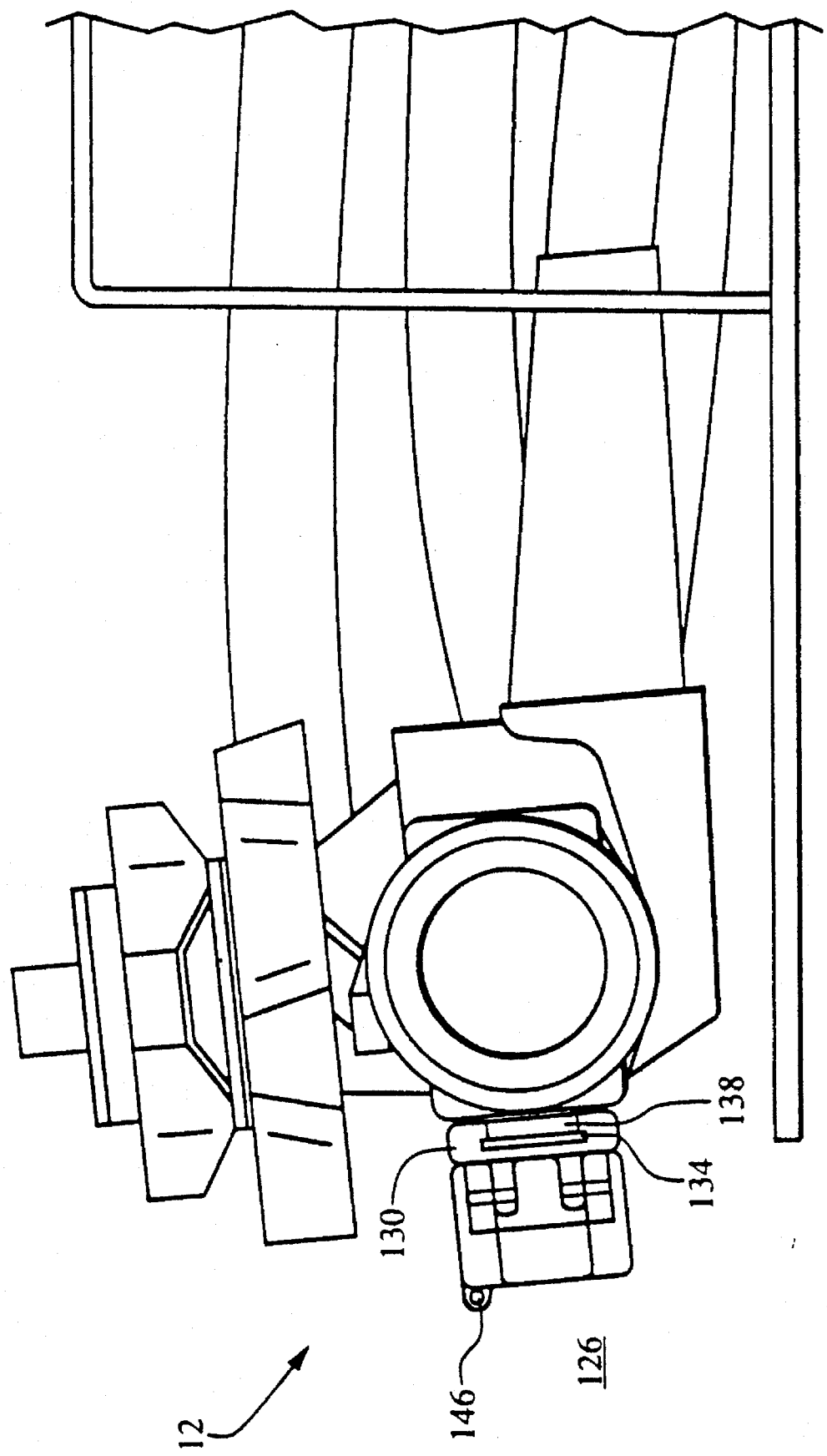
FIG. 11 is an end view of the connector FIG. 7 connected to the endoscope.

FIG. 11 illustrates housing 126 in an end view as it is coupled to the endoscope control section 12. The U-shaped clip or slidable fastening means 130 can be seen under flange 134 of the $CO_2$ valve 18 in FIG. 1 and around neck 138 thereof for attaching the housing 126 to the endoscope body portion 12.

Figure 13:
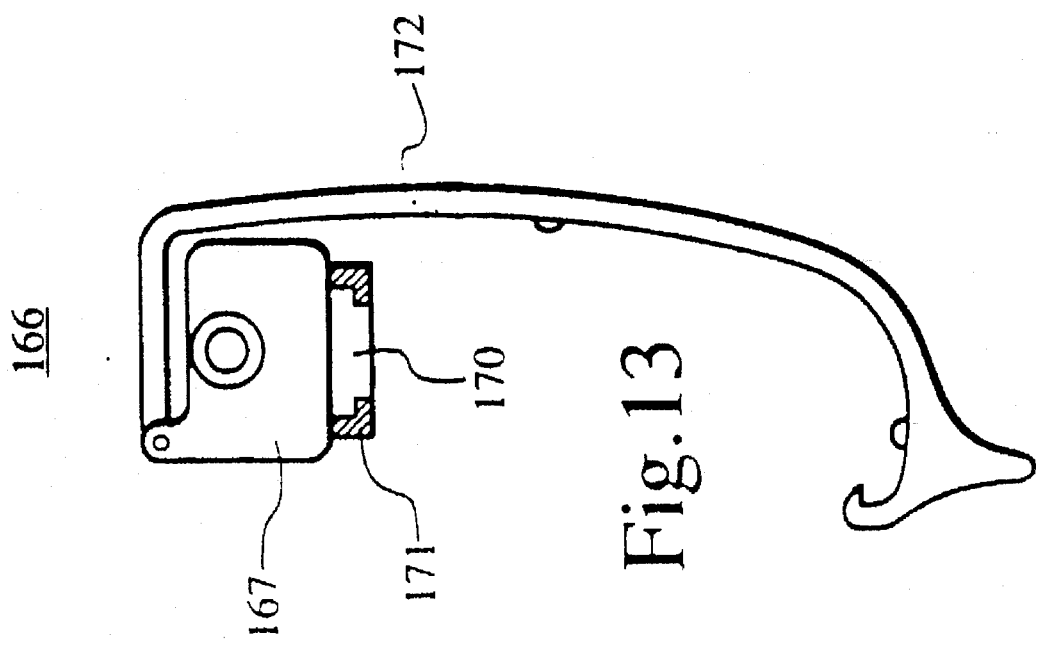
FIG. 13 is a rear view of the connector of FIG. 12.
Figure 12:
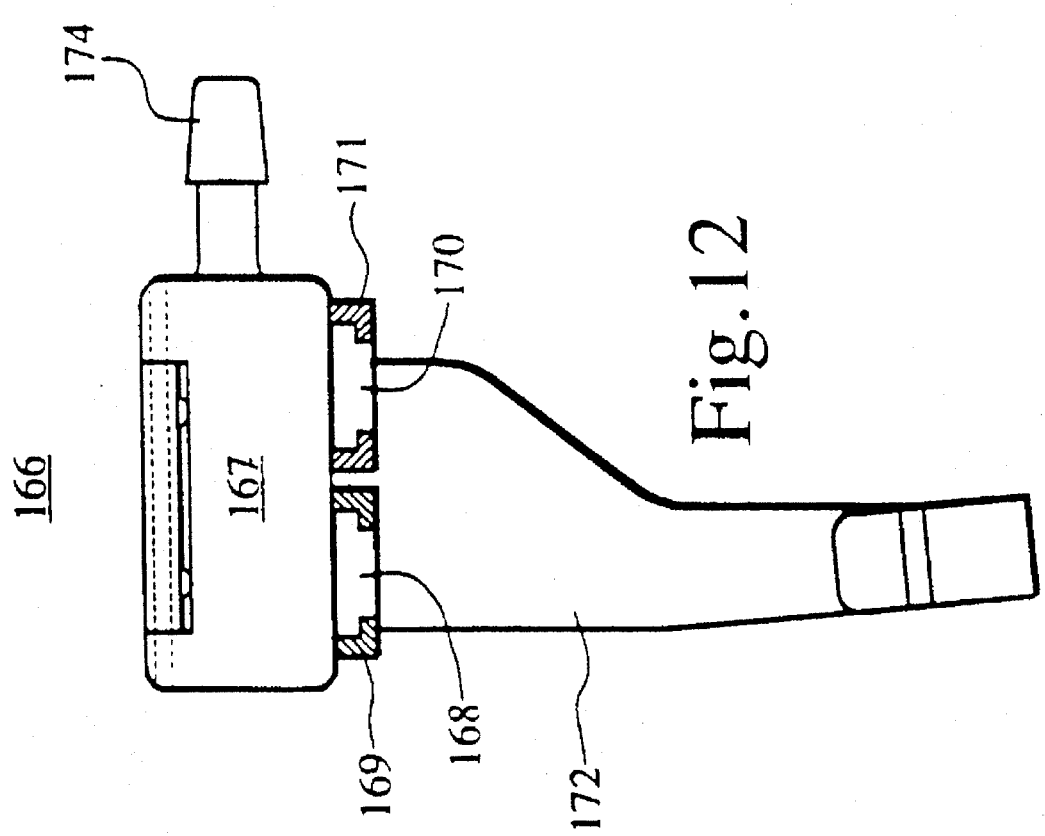
FIG. 12 is a side view of a two-port connector similar to that illustrated in FIG. 7.

For a two-port endoscope as illustrated in FIG. 2, the connector shown in FIGS. 12 and 13 can be utilized. The connector 166 simply has a hollow housing 167 with the two ports 168 and 170 that have rubber sealing devices 169 and 171 that form fluid-tight seal with the ports as described earlier in relation to the embodiment in FIG. 7. It also has a J-shaped extension 172 for holding the connector 166 in fluid-tight relationship with the endoscope body portion 12 as described earlier, and an extension 174 coupled to the interior 167. Extension 174 can be coupled to a suction source to pull sterilizing agent through the lumens of the endoscope. An end view of the device is shown in FIG. 13.

Figure 14:
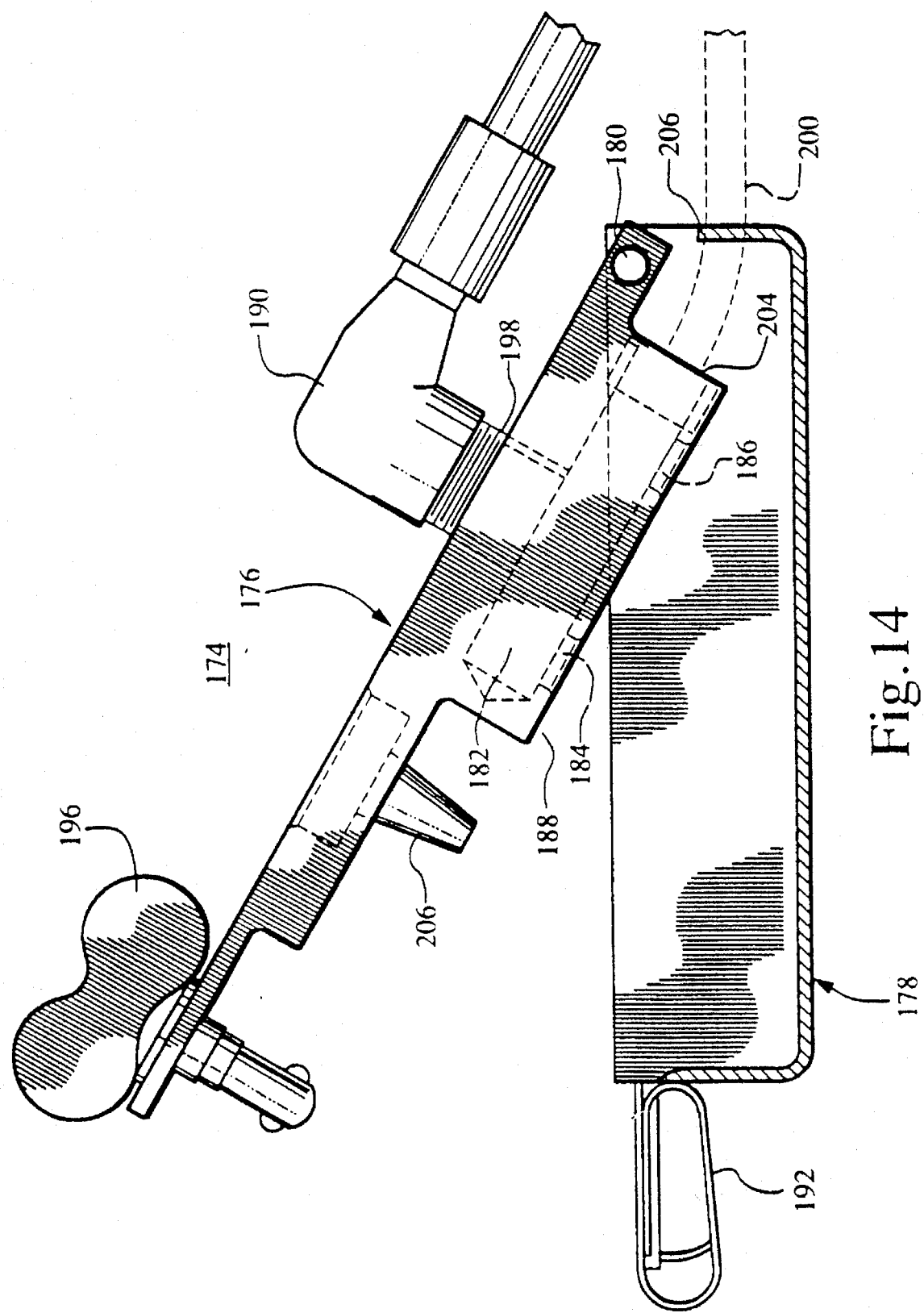
FIG. 14 is a side view of an alternate connector for a three-port endoscope.

An alternate embodiment of the connector is illustrated in FIG. 14. The alternate embodiment 174 has a hollow housing 176 that is pivotally attached to a rectangular base portion 178 at 180. The hollow housing portion 176 has a hollow interior 182 that is coupled to orifices 184 and 186 for mating with the endoscope ports 14 and 16 in FIG. 1 or FIG. 2. A pliable seal 188 on the housing surrounds the two orifices 184 and 186 and sits on the top flanges 154 and 156 (FIG. 10) of ports 14 and 16 of the endoscope in a fluid-tight relationship when the housing locked to the base 178. In this manner, minimum contact is made with the endoscope. The suction applied to line 190 to pull the sterilizing agent through the endoscope lumens and their output ports 14 and 16, through orifices 184 and 186 in the hollow housing 176 and out to the vacuum source. The base portion 178 provides the fastening means to attach the unit 174 to the endoscope. A spring clip 192 is attached to one end of base portion 178 under an orifice 194 illustrated in FIG. 16A. A one-quarter turn fastener 196 on a corresponding end of the housing 176 is in alignment with the clip orifice 194, such that when the housing 176 is pivoted downwardly about point 180 toward the base fastening means 178, the one-quarter turn fastener 196 is inserted in the orifice 194 and rotated one-quarter turn for attachment to the clip 192 in a well-known manner. When that is accomplished, the pliable seal 188 is compressed in sealing engagement with the endoscope and locks the connector 176 to the endoscope body. To obtain a lower profile device, a plug can be inserted in the orifice 198 and a flexible hose 200 connected to an orifice 204 such that the hose extends out an orifice 206 in the back of the rectangular base portion 178.

Figure 15A:
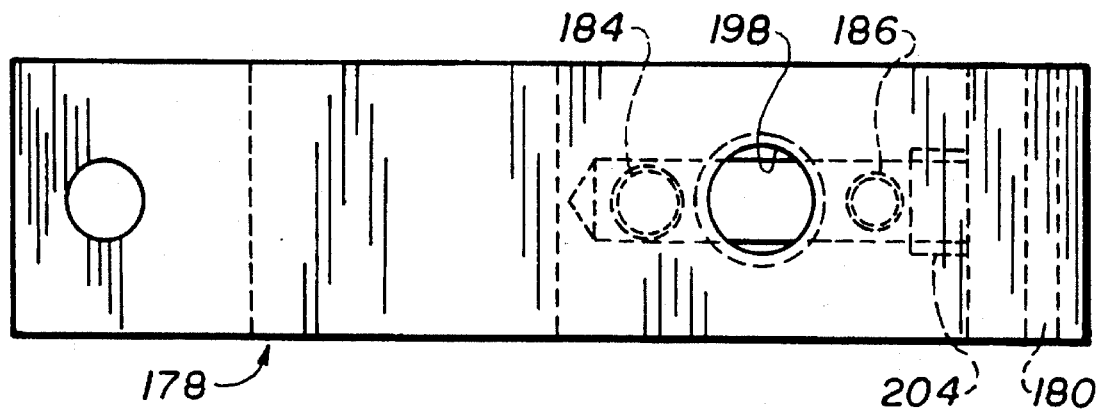
FIG. 15A is a top view of an alternate embodiment of the housing of the connector of FIG. 14 modified for a two-port connector.
Figure 15B:
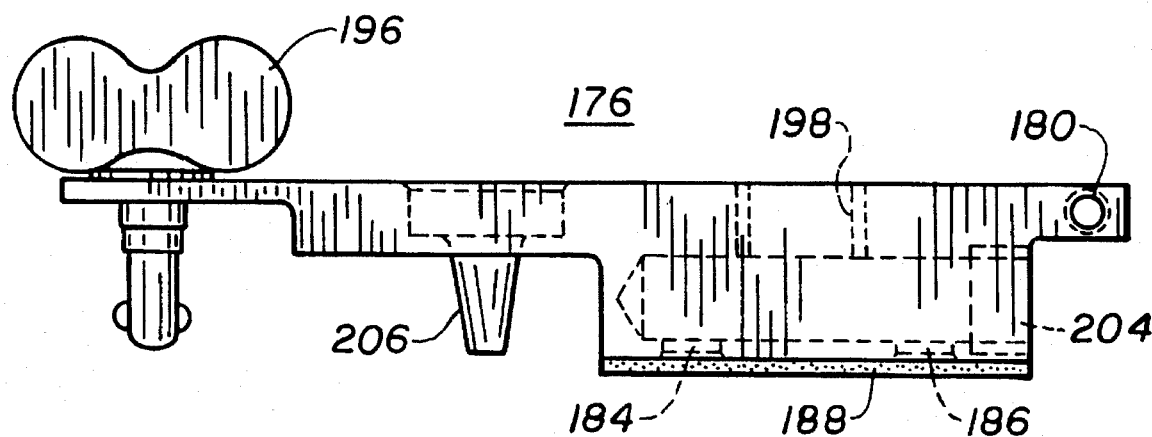
FIG. 15B is a side view of an alternate connector housing of FIG. 14 for a three-port endoscope.
Figure 15C:
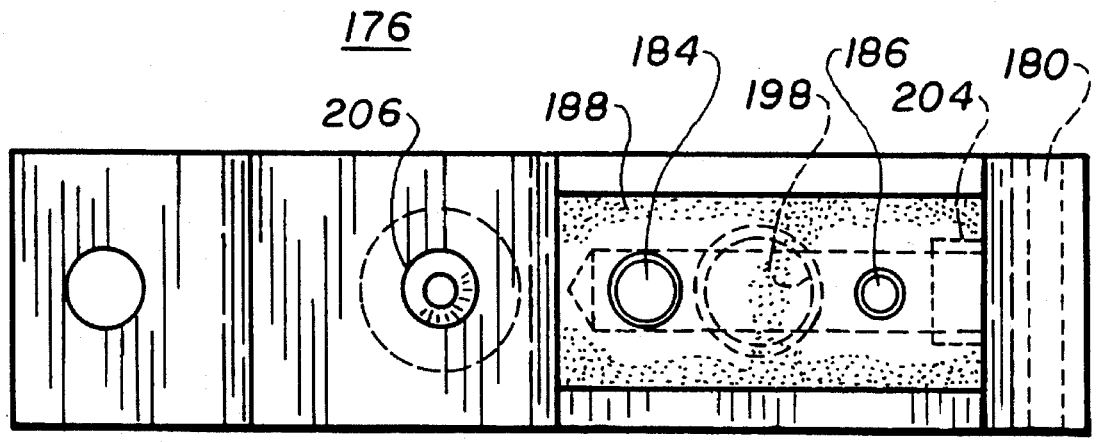
FIG. 15C is a bottom view of the alternate connector housing illustrated in FIG. 15B.

A top view of the housing 176 for a two-port endoscope is illustrated in FIG. 15A. It has a hollow chamber 182 with orifices 184 and 186 communicating with the hollow interior 182. Output orifices 198 and 204 are both illustrated and, as indicated earlier, the suction can be taken from either of those orifices with the other being plugged. The same unit in FIG. 15A can be used for a three-port endoscope simply by adding the $CO_2$ valve depressor 206 as illustrated in FIG. 14 and FIG. 15B. A bottom view of the three-port device in FIG. 15B is illustrated in FIG. 15C. For simplicity of the drawings, the one-quarter turn fastener 196 not illustrated in FIG. 15A or 15C. Note seal 188 that extends around orifices 184 and 186.

Figure 16A:
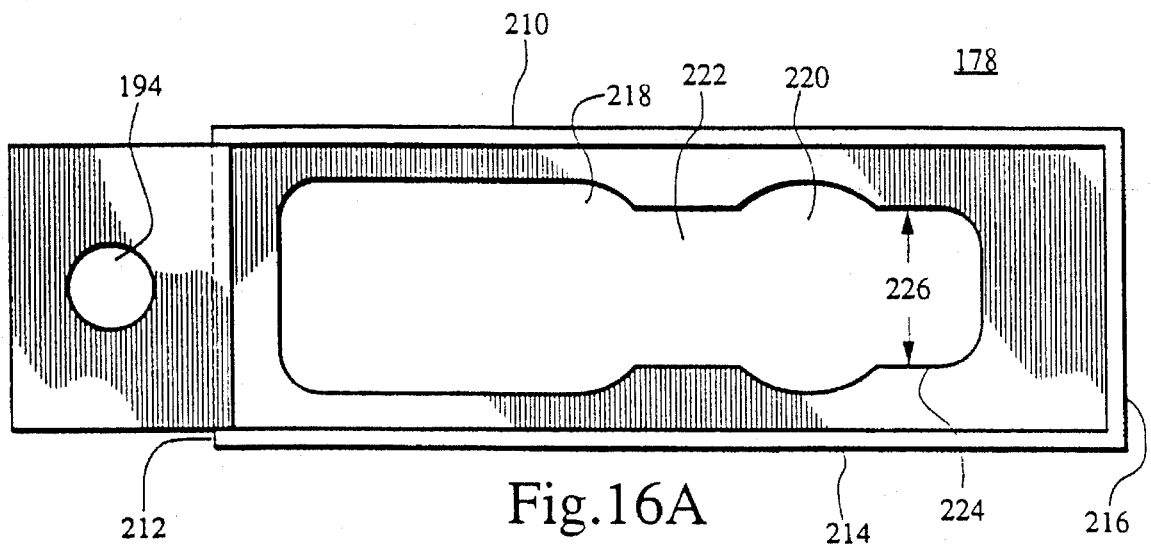
FIG. 16A is a plan view of the base portion of the alternate two or three-port connector illustrated in FIGS. 15A and 15B.
Figure 16B:
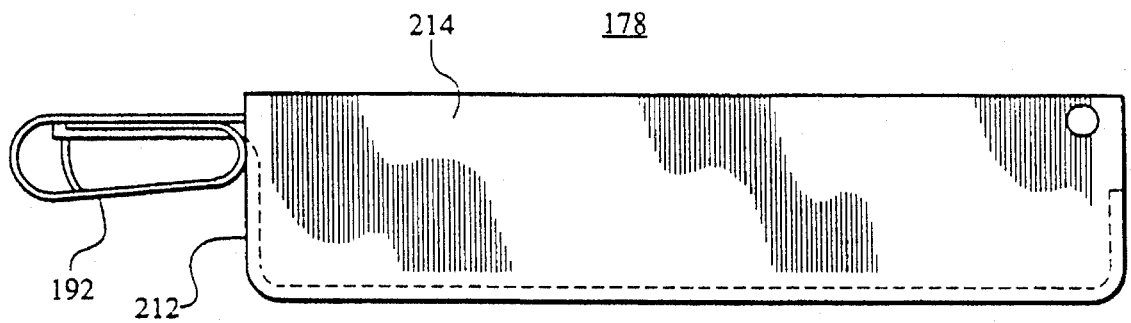
FIG. 16B is a side view of the base portion illustrated in FIG. 16A.

A top view of the base portion 178 is illustrated in FIG. 16A. It is a rectangular base portion having four vertical side walls 210, 212, 214 and 216 integrally formed therewith. Openings 218 and 220 in the base receive the two ports 14 and 16 of the endoscope illustrated in FIG. 1. A slot 222 and 224 on one side of each of the openings 218 and 220 has width 226 sufficient to slide under the port flanges 154 and 156 shown in FIG. 10, thus coupling the base 178 to the endoscope body. A side view of the base portion 178 is illustrated in FIG. 16B. When the housing 176 is pivoted downwardly and latched to the base portion 178 with fastener 196, the seal 188 compressed and the pressure locks the base to the endoscope ports 14 and 16.

Figure 17:
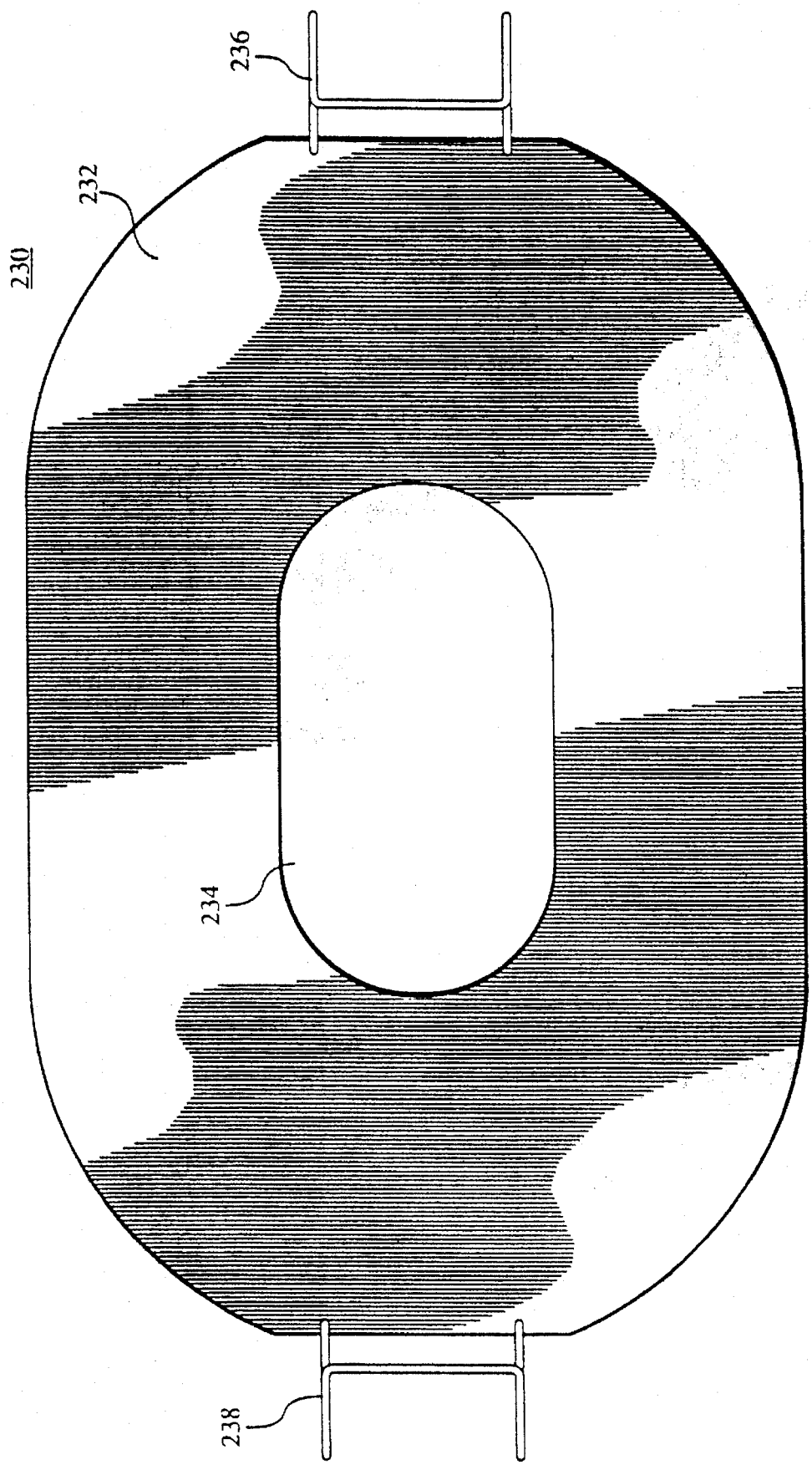
FIG. 17 is a plan view of a tray for holding an endoscope to be placed in a cassette.

A tray 230 for holding the endoscope in the cassette is illustrated in FIG. 17. It comprises, in one example, a flat plastic sheet 232 having an oval orifice 234 for receiving the cassette center support illustrated in FIGS. 4B and 4C. It also has opposing handles 236 and 238 on opposite ends thereof for handling the tray which could also serve to secure the tray in a fixed position when enclosed in a cassette.

Figure 18:
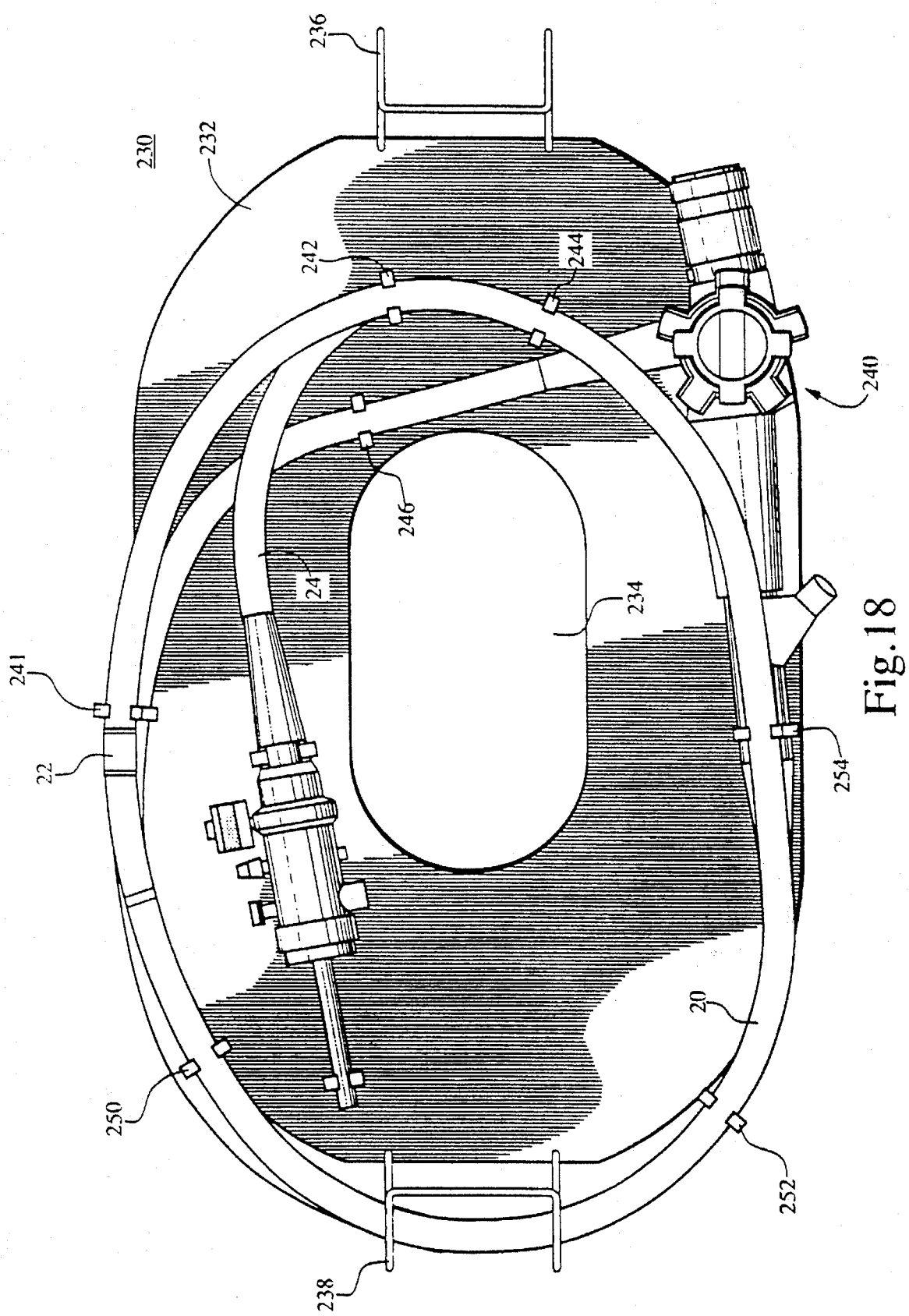
FIG. 18 is a plan view of the tray in FIG. 17 illustrating an endoscope attached thereon.

FIG. 18 is a plan view of the tray 230 with an endoscope 240 mounted thereon prior to being placed in the cassette. It will be noted that clips 242–254 hold the endoscope tubes 20 and 24 to the tray 230 in fixed relation with respect to each other. This can be seen more clearly in the side view in FIG. 19 in which the clips 252 and 254 are shown separating the loops of the insertion tube 20 and the universal cord or tube 24. Thus, the sterilizing agent can make maximum contact with the hoses 20 and 24, whereas if they were not held in spaced relationship by the clips on the cassette tray they would be in contact with each other for extended distances, thus leaving some areas that could not be sterilized. The tray 232 allows the endoscope 240 to be positioned in the clips 242–254 prior to being placed in the cassette for sterilization. It also allows the tray to be removed from the cassette in the operating room when ready for use.

Figure 20:
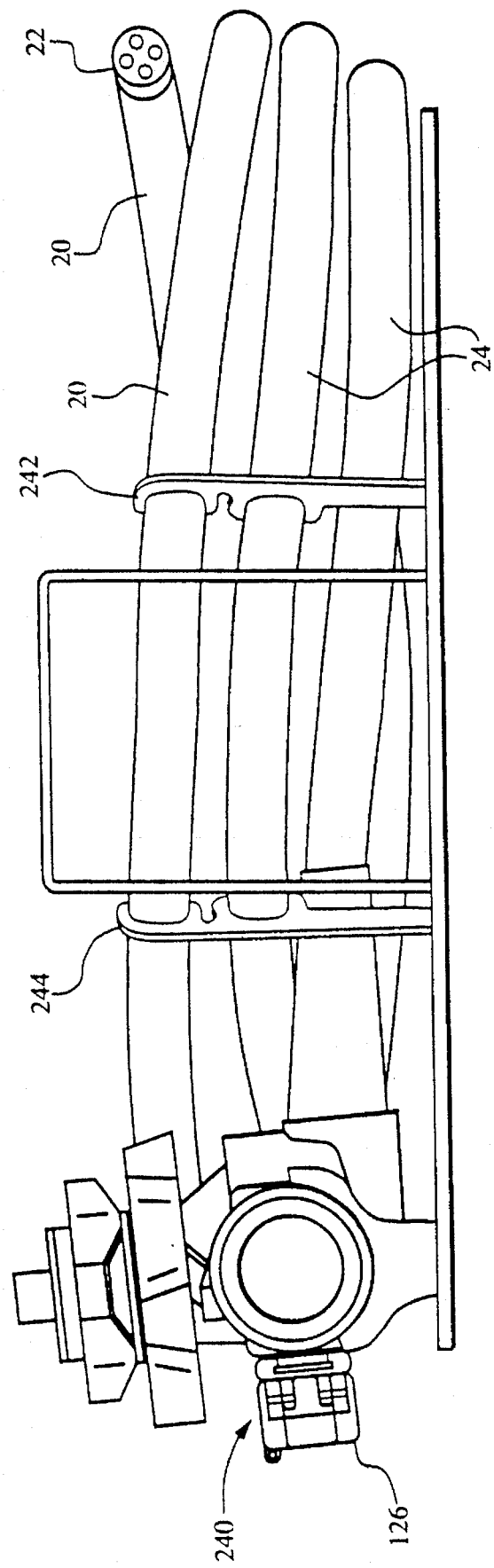
FIG. 20 is an end view of the tray in FIG. 19 holding the endoscope.

FIG. 20 is an end view of the cassette tray with the endoscope 240 thereon illustrating the clips 242 and 244 holding the tubes 20 and 24 in spaced relationship with each other and to themselves as they will be when they are being sterilized.

FIG. 21 is a side view of a cassette 44 in its sealed condition with the endoscope on the tray inside the cassette. A partial cutaway section illustrates the wall of the oval center support designated by the numeral 260 in this figure. Since the cassette 44 is formed of clear plastic, the endoscope and tray can be seen through the cassette sections 262 and 264 without unsealing the cassette sections.

While in the foregoing there has been disclosed embodiments of the invention in considerable detail for purposes of illustration, it will be understood by those skilled in the art that many of these details may be varied without departing from the spirit and scope of the invention.

We claim:

1. A device utilizing a sterilizing agent to sterilize a lumened object, said lumened object having a part having a neck portion and an outer flange at the top of said neck portion, said device comprising:

a cassette for containing said lumened object, said cassette comprising;

a first container section;

a second container section engaged with said first container section;

a fluid-tight inner cavity formed between said first container section and said second container section; and an input port in the casseette for receiving a sterilizing agent into said inner cavity;

an output port, separate from said input port, said output port connectable to a vacuum source and including a passage through which the sterilizing agent is expelled from said inner cavity; and a connector having a first connecting portion connectable to said lumened object and a second connecting portion connectable to said output port; said first connecting portion comprising a seal for creating a fluid-tight connection about said neck portion of said port of said lumened object;

whereby said lumened object is connected to said connector and said connector is connected to said outport port and the first container section is engaged with the second container section to form said fluid-tight inner cavity in which the lumened object is retained; sterilizing agent is introduced through said input port into said inner cavity where it sterilizes the outside surface of the endoscope and a vacuum is applied to the output port and the sterilizing agent is expelled from the inner cavity by passing through a lumen of the lumened object, thereby sterilizing the lumen, and passing through the passage and out of said cassette.

2. A device as described in claim 1 wherein said first connecting portion defines a hollow cavity therein, said connector not including a projection or extension for insertion into said lumened object.

3. A device as defined in claim 1 wherein said input port further comprises a first valve for automatically opening and closing said input port, and said output port further comprises a second valve for automatically opening and closing said output port, each of said valves having an open position and a closed position, wherein said first valve moves from said closed to open position upon engagement of said input port with a source of sterilizing agent, said first valve returning to said closed position upon removal from said source of sterilizing agent, and said second valve moves from said closed to said open position upon engagement of said output port with a vacuum source, said second valve returning to said closed position upon removal from said vacuum source.

4. A method for sterilizing and storing endoscopes comprising the steps of:

a) providing one or more endoscopes, each of said endoscopes including an outer surface and at least one lumen;

b) providing a sealable cassette comprising:
      i) a first container section;
      ii) a second container section engagable with said first container section;
      iii) an input port; and
      iv) an output port; and c) providing a connector for connecting the one or more endoscopes to said output port;

d) connecting an end of each of the endoscope(s) to said connector;

e) connecting said connector to said output port;

f) engaging said first container section with said second container section to create a fluid-tight inner cavity therebetween, said one or more endoscopes being enclosed within said fluid-tight inner cavity;

g) introducing a gaseous sterilizing agent into said inner cavity through said input port to sterilize the outer surface of said one or more endoscopes;

h) applying a vacuum to said output port and expelling the gaseous sterilizing agent within said inner cavity by drawing the gaseous sterilizing agent through the endoscope(s) lumen(s) at subatmospheric pressure and through said connector and through said output port and out of said inner cavity.

5. A method as defined in claim 4 wherein said input port further comprises a first valve for automatically opening and closing said input port, and said output port further comprises a second valve for automatically opening and closing said output port, each of said valves having an open position and a closed position, wherein said first valve moves from said closed position to said open position upon engagement with a source of sterilizing solution, said first valve returning to said closed position upon removal from said source of sterilizing solution, and said second valve moves from said closed position to said open position upon engagement with a vacuum source, said second valve returning to said closed position upon removal from said vacuum source connector and through the passage of said output port and out of said cassette.

6. A method for sterilizing and storing endoscopes comprising the steps of:

a) providing one or more endoscopes, each of said endoscopes including an outer surface and at least one lumen;

b) providing a sealable cassette comprising:
      i) a first container section;
      ii) a second container section engagable with said first container section;
      iii) an input port;

iv) an output port comprising a connector; and c) connecting an end of each of the endoscope(s) to said connector;

d) engaging said first container section with said second container section to create a fluid-tight inner cavity therebetween, said one or more endoscopes being enclosed within said fluid-tight inner cavity;

e) introducing a gaseous sterilizing agent into said inner cavity through said input port to sterilize the outer surface of said one or more endoscopes;

f) applying a vacuum to said output port and expelling the gaseous sterilizing agent within said inner cavity by drawing the gaseous sterilizing agent through the endoscope(s) lumen(s) at subatmospheric pressure and through said connector and through said output port and out of said inner cavity.

7. A method for sterilizing and storing a lumened object, said method comprising the step of:

a) providing a lumened object, said object including an outer surface and at least one lumen;

b) providing a sealable cassette comprising:
  i) a first container section;
  ii) a second container section engagable with said first container section;
  iii) an input port;
  iv) an output port comprising a connector; and c) connecting an end of the lumened object to said connector;

d) engaging said first container section with said second container section to create a fluid-tight inner cavity therebetween, said lumened object being enclosed within said fluid-tight inner cavity;

e) introducing a gaseous sterilizing agent into said inner cavity through said input port to sterilize the outer surface of said lumened object; and f) applying a vacuum to said output port and expelling the gaseous sterilizing agent within said inner cavity by drawing the gaseous sterilizing agent through the lumen(s) of the object at subatmospheric pressure and through said connector and through said output port and out of said inner cavity.

\* \* \* \* \*